US008678238B2

(12) United States Patent
Brunk et al.

(10) Patent No.: US 8,678,238 B2
(45) Date of Patent: Mar. 25, 2014

(54) SELF-CONTAINED HAND-HELD YOKE-CONNECTED DEVICE FOR DISPENSING A TWO-PART ADHESIVE AEROSOL

(75) Inventors: Donald H. Brunk, Boothwyn, PA (US); William Gerald Dimaio, Jr., Boothwyn, PA (US)

(73) Assignee: Actamax Surgical Materials, LLC, Berkeley, CA (US)

( * ) Notice: Subject to any disclaimer, the term of this patent is extended or adjusted under 35 U.S.C. 154(b) by 754 days.

(21) Appl. No.: 12/850,745

(22) Filed: Aug. 5, 2010

(65) Prior Publication Data

US 2012/0032000 A1 Feb. 9, 2012

Related U.S. Application Data

(63) Continuation of application No. 12/827,372, filed on Jun. 3, 2010, now abandoned.

(51) Int. Cl.

| | |
|---|---|
| ***B67D 7/70*** | (2010.01) |
| ***B05B 7/02*** | (2006.01) |
| ***B05B 9/01*** | (2006.01) |
| ***A62C 13/62*** | (2006.01) |
| ***A62C 13/66*** | (2006.01) |
| ***A62C 35/58*** | (2006.01) |
| ***B05B 9/03*** | (2006.01) |
| ***A61M 37/00*** | (2006.01) |

(52) U.S. Cl.
USPC ............ 222/137; 239/525; 239/302; 604/191

(58) Field of Classification Search
USPC ................. 222/137, 261–263, 309, 135, 258; 604/82, 91, 191; 239/525, 528, 302, 239/320, 337, 418
See application file for complete search history.

(56) References Cited

U.S. PATENT DOCUMENTS

| | | | | | |
|---|---|---|---|---|---|
| 3,841,555 | A | * | 10/1974 | Lilja | 239/8 |
| 4,359,049 | A | | 11/1982 | Redl et al. | |
| 4,631,055 | A | | 12/1986 | Redl et al. | |
| 4,902,281 | A | * | 2/1990 | Avoy | 604/191 |
| 5,166,315 | A | | 11/1992 | Summerton et al. | |
| 5,582,596 | A | | 12/1996 | Fukunaga et al. | |
| 5,656,035 | A | * | 8/1997 | Avoy | 604/191 |
| 5,665,067 | A | * | 9/1997 | Linder et al. | 604/82 |
| 5,722,950 | A | * | 3/1998 | Fujita et al. | 604/48 |
| 5,989,215 | A | | 11/1999 | Delmotte et al. | |
| 6,059,749 | A | * | 5/2000 | Marx | 604/82 |

(Continued)

FOREIGN PATENT DOCUMENTS

EP 0835667 B 11/2005

*Primary Examiner* — Len Tran
*Assistant Examiner* — Chee-Chong Lee
(74) *Attorney, Agent, or Firm* — McCarter & English

(57) ABSTRACT

A self-contained, hand-held spray dispensing device includes an internal source of pressurized fluid that exerts a motive force on a pair of liquid ejecting elements to cause each to eject a liquid into a discharge line. The liquids remain separated until each exits its discharge port. A pressurized fluid is directed over the outlet ends of the discharge line beginning before a flow interrupter in the discharge line is opened to permit flow therethrough and ceasing after liquid flow is terminated. The pressurized fluid flow over the outlet of the discharge line aerosolizes liquids emanating from the outlet ends. The liquid ejecting element is connected to a force transmitting yoke. The yoke responds to pressurized fluid from the source to generate the motive force on the ejecting element.

25 Claims, 16 Drawing Sheets

(56) References Cited

U.S. PATENT DOCUMENTS

| | | | | |
|---|---|---|---|---|
| 6,165,201 | A | 12/2000 | Sawhney et al. | |
| 6,179,862 | B1 | 1/2001 | Sawhney | |
| 6,454,786 | B1 * | 9/2002 | Holm et al. | 606/214 |
| 6,461,325 | B1 * | 10/2002 | Delmotte et al. | 604/82 |
| 6,565,539 | B1 * | 5/2003 | Zinger et al. | 604/191 |
| 6,673,093 | B1 | 1/2004 | Sawhney | |
| 6,874,657 | B2 * | 4/2005 | Metzner et al. | 222/82 |
| 7,217,254 | B2 * | 5/2007 | Kirwan et al. | 604/82 |
| 2007/0213683 | A1 | 9/2007 | Cassingham et al. | |
| 2008/0121657 | A1 * | 5/2008 | Voegele et al. | 222/137 |

* cited by examiner

Continued on Fig. 4C

Continued from Fig. 4A

Continued from Fig. 4A
FIG. 4C
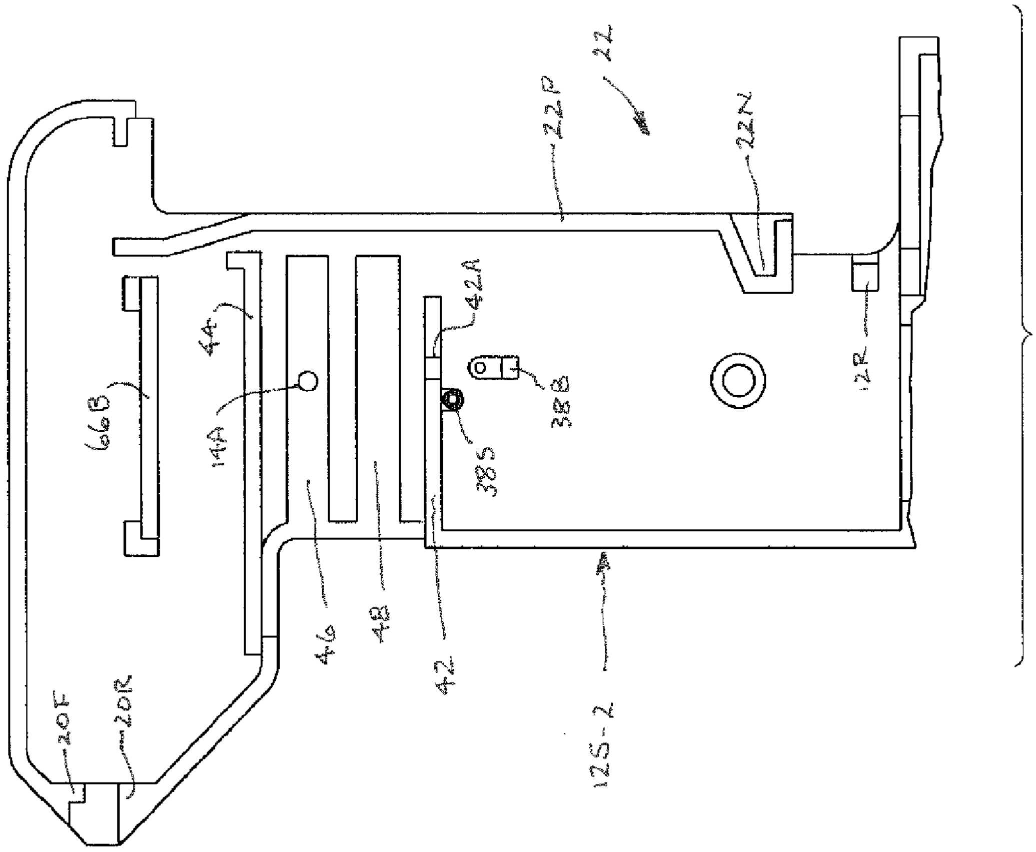
Continued on Fig. 4D

SELF-CONTAINED HAND-HELD YOKE-CONNECTED DEVICE FOR DISPENSING A TWO-PART ADHESIVE AEROSOL

CROSS-REFERENCE TO RELATED APPLICATION

This application is a continuation of U.S. application Ser. No. 12/827,372, filed Jun. 30, 2010, which is incorporated herein in its entirety by reference and made a part thereof.

Subject matter disclosed herein is disclosed and claimed in the following copending application, filed contemporaneously herewith and assigned to the assignee of the present invention:

Self-Contained Hand-Held Direct Drive Device For Dispensing A Two-Part Adhesive Aerosol (CL-5122).

BACKGROUND OF THE INVENTION

1. Field of the Invention

This invention relates to a sprayer device used in the dispensing of at least one but preferably two liquids, such as the components of a fast-setting adhesive aerosol.

2. Description of the Prior Art

A fast-setting two-component adhesive is an adhesive compound that cures within seconds of the components being mixed together. Such fast-setting two-component adhesives have many applications, including use as tissue adhesives for a number of potential medical applications. Such potential medical applications include closing topical wounds, delivering drugs, providing anti-adhesion barriers to prevent post-surgical adhesions, and supplementing or replacing sutures or staples in internal surgical procedures. To be suitable for medical applications such tissue adhesives must be fast-curing, have good mechanical strength, be able to bind to the underlying tissue and pose no risk of infection.

The components of such fast-setting two-component adhesives must be mixed either at the site of application or immediately (i.e., typically within a few seconds) before application.

One conventional technique employs a static mixer connected to the discharge ends of the containers holding the liquid components and moving these components through a serpentine passage to the tissue being treated. The components are mixed in the serpentine passage before the adhesive exits the passage. Representative of such conventional static mixer are those devices sold by Med Mix Systems AG, Rotkreuz, Switzerland and Mix Tek System LLC, New York, N.Y. U.S. Pat. No. 5,595,712, assigned to the assignee of the present invention, also discloses a static mixing device employing a serpentine passage within a planar structure.

Prior art static mixers are believed disadvantageous for use in any medical application which requires intermittent application of adhesive. If flow of the adhesive through the mixer is interrupted, even momentarily, the mixed components increase in viscosity. This increase in viscosity, known as gelling, may occur so rapidly that the mixer passage becomes clogged, thus preventing the resumption of flow of the adhesive.

Besides the static mixers, dynamic mixers such as powered impellers and magnetic stir bars have been used. However these devices are costly and cumbersome and not particularly amenable to medical use as they may damage the adhesive by over-mixing.

Hand-held mixing devices that entrain the liquid components in a gas stream are also known. Some of these devices join the liquid components in a common discharge line prior to application to the site and are thus subject to the same risk of gelling as in a static mixer.

Other hand-held mixing devices use separate discharge lines for each of the liquid components. In these cases a gas entrains each liquid and carries the liquid through a separate discharge line. However, when the device is used with relatively high viscosity liquids of the type used in some adhesives (ranging in viscosity from about ten to one thousand centipoise) the liquid deposits appear on the deposit site as segregated clumps which are not well mixed.

Neither of these gas powered devices are self-contained since the gas used in both hand-held devices is supplied through a tethered connection to a fluid source. Such a tethered arrangement is believed disadvantageous because it limits the ease with which an operator can handle the device.

Accordingly, in view of the foregoing there is believed to be a need for a self-contained, hand-held dispensing device capable of delivering two well-mixed liquid components directly to a desired site while avoiding the clogging problems of prior art devices.

SUMMARY OF THE INVENTION

The present invention is directed toward a self-contained, hand-held spray dispensing device for dispensing one or more liquid material(s). Preferably, the dispensing device is useful to dispense a spray containing a mixture of two liquid materials, such as the components of a fast-setting two-part adhesive, onto a site.

The dispensing device of the present invention is able to receive and to support at least one, but more preferably two, container(s) each having a discharge port therein and a liquid ejecting element associated therewith.

In a first type of a container with which a first embodiment of the invention may be used, the liquid ejecting element is connectable to a force transmitting yoke. The yoke has an actuating disc with a working surface thereon. The liquid ejecting element may be positioned to operate on either the interior or the exterior of the container.

A container of a second type (wherein the liquid ejecting element is received within the container) may be used with a second embodiment of the invention. In this case the end of the container is closed by an end cap with a fluid passage therethrough. With a container of this type the liquid ejecting element has the working surface thereon.

In the preferred instance of either embodiment the liquid ejecting element takes the form of a piston movably disposed on the interior of a container. Each piston is able to respond to a motive force imposed thereon to displace within its container, thereby to cause a liquid material in that container to be ejected through the discharge port.

The dispensing device includes a housing that has a first and a second liquid discharge line disposed therein. Each liquid discharge line has an inlet end and an outlet end. A flow interrupter is connected within the liquid discharge lines for controlling the passage of liquid material therethrough.

A container support arrangement is provided within the housing. The container support arrangement is able to receive and to support a first and a second liquid container (of either type) within the housing such that the discharge port of each container is disposed in fluid communication with the inlet end of a liquid discharge line. The container(s) (and the force transmitting yoke, if needed) may be removable from the container support arrangement after use.

A cartridge support arrangement that includes a bottom closure is disposed within the housing. The cartridge support arrangement is able to receive and to support a cartridge holding a pressurized fluid, such as carbon dioxide gas. By providing a support arrangement for a motive fluid cartridge internal to the housing, the dispenser is able to be self-contained and easily handled by an operator, and the need for a tethered connection eliminated. The cartridge may be removable from the cartridge support arrangement after use.

In the first embodiment of the dispensing device an actuator is disposed within the housing. The actuator is sized to receive therein an actuating disc of a force transmitting yoke. In this embodiment a first pressurized fluid line is connected between a cartridge receivable within the housing and the actuator cylinder and into fluid communication with the working surface of a plunger so that a motive force may be applied to the actuating disc of the yoke.

In the second embodiment of the dispensing device the first pressurized fluid line extends from a cartridge receivable within the housing to the fluid passage in the end cap of each container and, thus, directly into fluid communication with the working surface of the piston.

A second pressurized fluid line within the housing connects the cartridge into fluid communication with the outlet end of each liquid discharge line. A valve controls the flow of pressurized fluid through the first and the second pressurized fluid lines.

A trigger is operatively associated with both the valve and the flow interrupter. The trigger is movable from a rest position to a first operational position. When in the first operational position the trigger opens the valve to permit simultaneous pressurized fluid flow through both pressurized fluid lines. The pressurized fluid flow through the first line acts on the working surface of a plunger or on the working surface of the piston of a container received within the housing, as the case may be, thereby to impose a motive force on each piston to eject a liquid in the container through its discharge port. The flow through the second line provides a flow of fluid over the outlet ends of the liquid discharge lines.

The trigger is sequentially movable from the first operational position to a second operational position. In the second operational position the flow interrupter is opened to permit the passage of a liquid material through each liquid discharge line. Liquid material emanating from the outlet ends of the liquid discharge lines is aerosolized by the pressurized fluid flow from the second pressurized fluid line.

With the spray dispensing device of the present invention the two liquid materials are isolated from each other until they exit the outlet ends of the liquid discharge lines, thus avoiding any possibility of premature reaction of the liquids with each other. At a region spaced away from the outlet ends of the discharge lines the liquids are aerosolized into droplets by an annular stream of pressurized fluid flow from the second pressurized fluid line. The aerosolized liquid streams intermix with each other as they transit toward the target site, thus avoiding the clogging problems associated with prior art dispensing devices.

A spray dispensing device in accordance with either embodiment of the present invention may form a part of a kit for dispensing liquid materials. The kit may include a cartridge having a pressurized fluid therein, and/or one or more containers (of either type) having a liquid material therein.

BRIEF DESCRIPTION OF THE DRAWINGS

The invention will be more fully understood from the following detailed description taken in connection with the accompanying drawings, which form a part of this application, and in which:

FIGS. 4C and 4D taken together are a complementary composite elevation view of the interior surface of the other shell of the housing of the hand-held spray dispensing device, with the paired FIGS. 4A/4B and 4C/4D being oriented such that the shells are illustrated in booked relationship with each other;

FIG. 6A is a top section view showing the hand-held spray dispensing device of FIGS. 4A through 4D taken along section lines 6A-6A therein, while

Figure 4A:
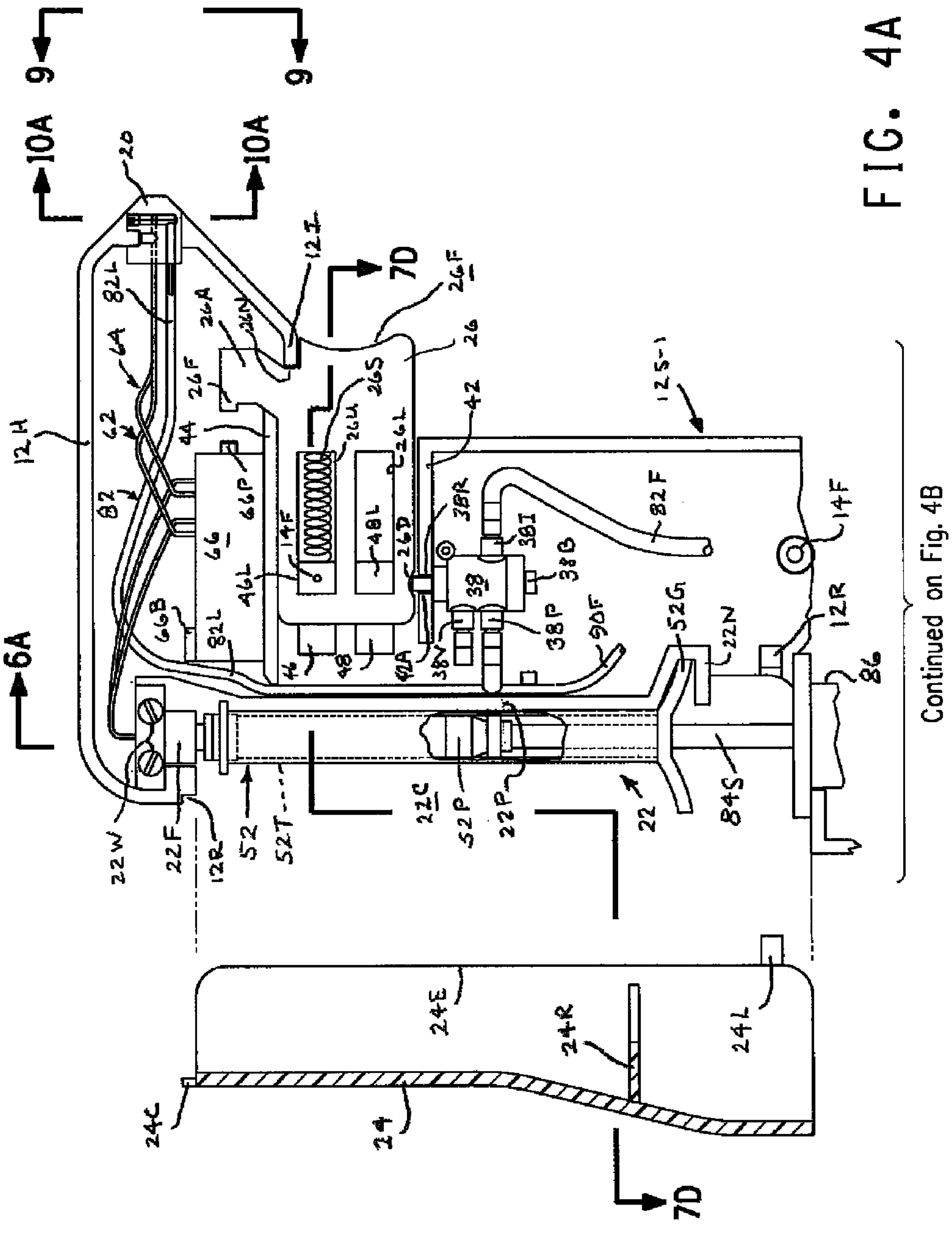
FIGS. 4A and 4B taken together show a composite elevation view of the interior of one shell of the housing of the hand-held spray dispensing device of FIG. 1 illustrating the disposition of various operational elements therein in accordance with a first embodiment of the present invention.
Figure 5A:
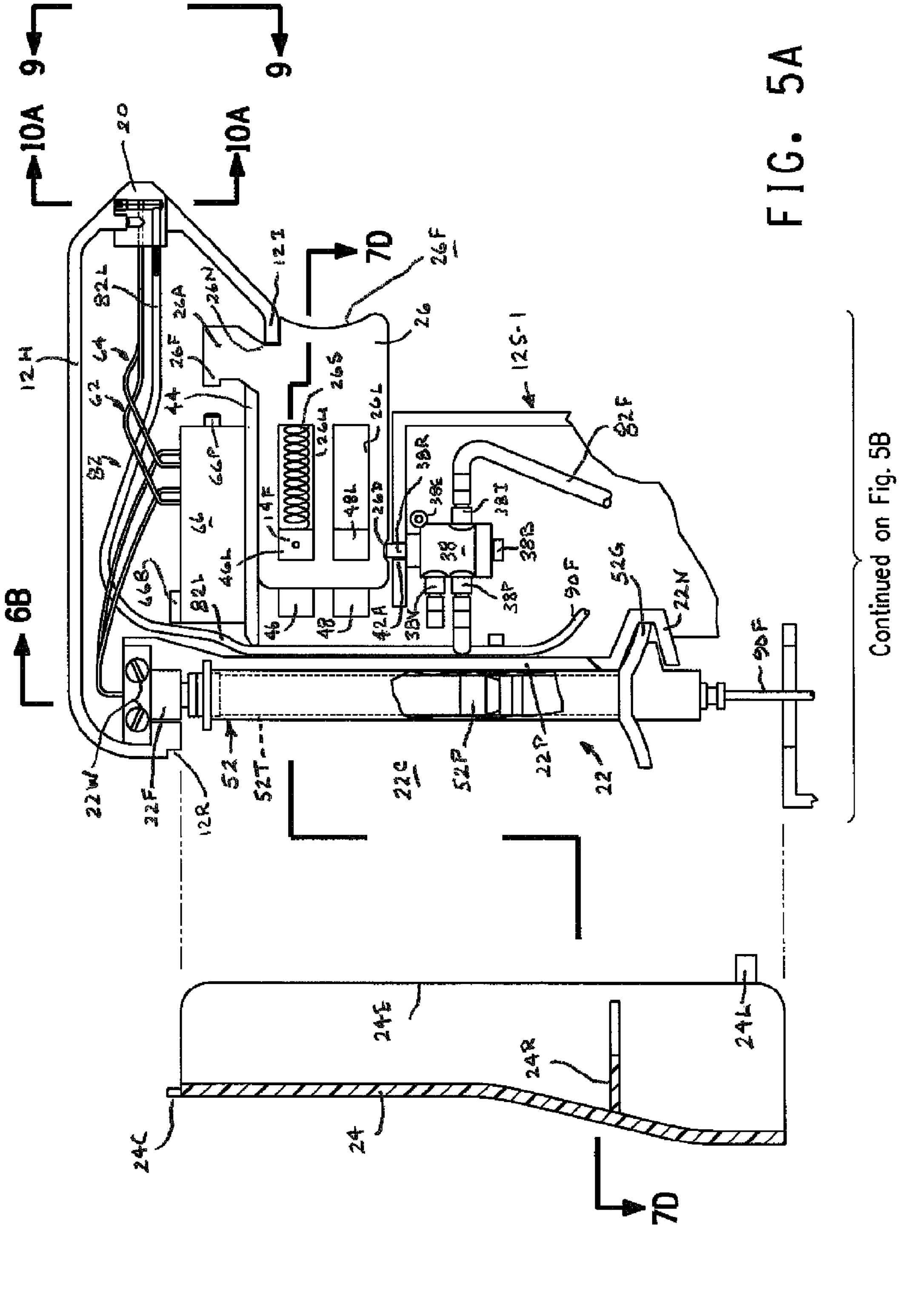
FIGS. 5A and 5B are views similar to FIGS. 4A and 4B which taken together show a composite elevation view of the interior surface of one shell of the housing of a hand-held spray dispensing device in accordance with a second embodiment of the present invention.
Figure 7B:
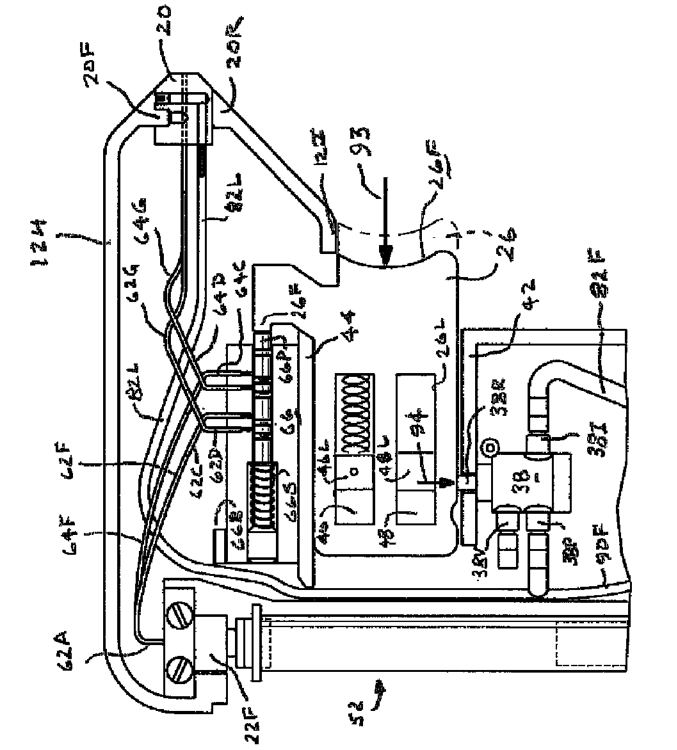
FIGS. 7A through 7D are side elevation views illustrating the interactions between the operating trigger of the device and the liquid flow interrupter whereby the flows of liquid adhesive components and aerosolizing gas is controlled in accordance with the present invention, it being understood that section hatching of various of the elements is omitted for clarity of illustration.
Figure 7A:
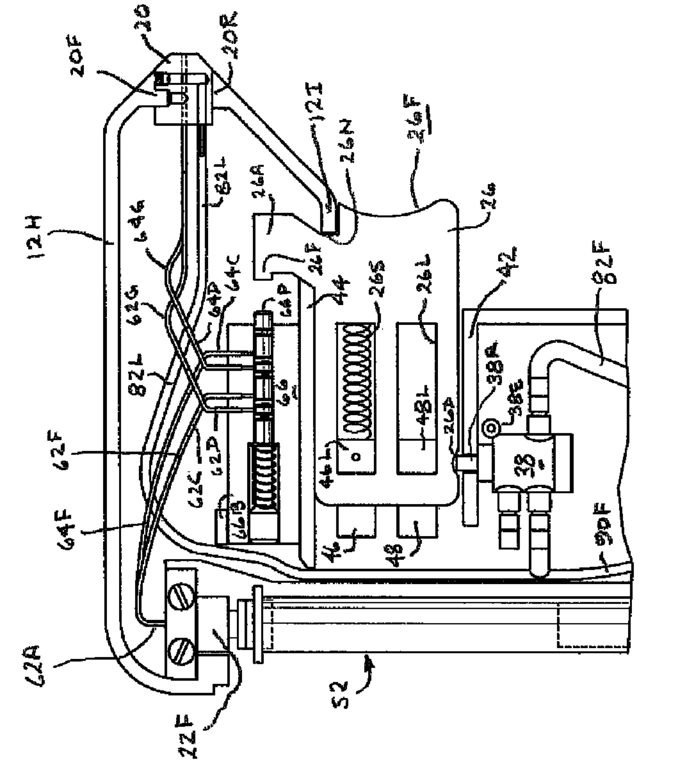
Figure 7D:
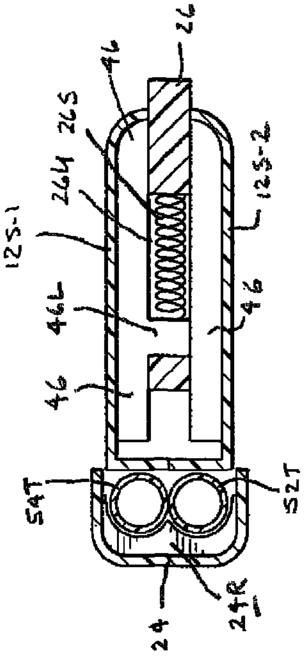
Figure 7C:
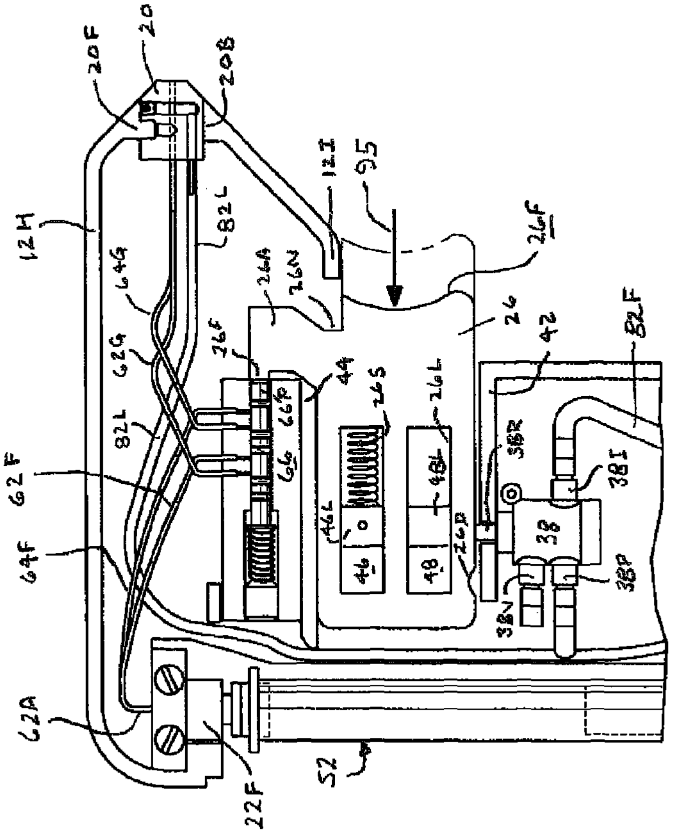
Figure 8A:
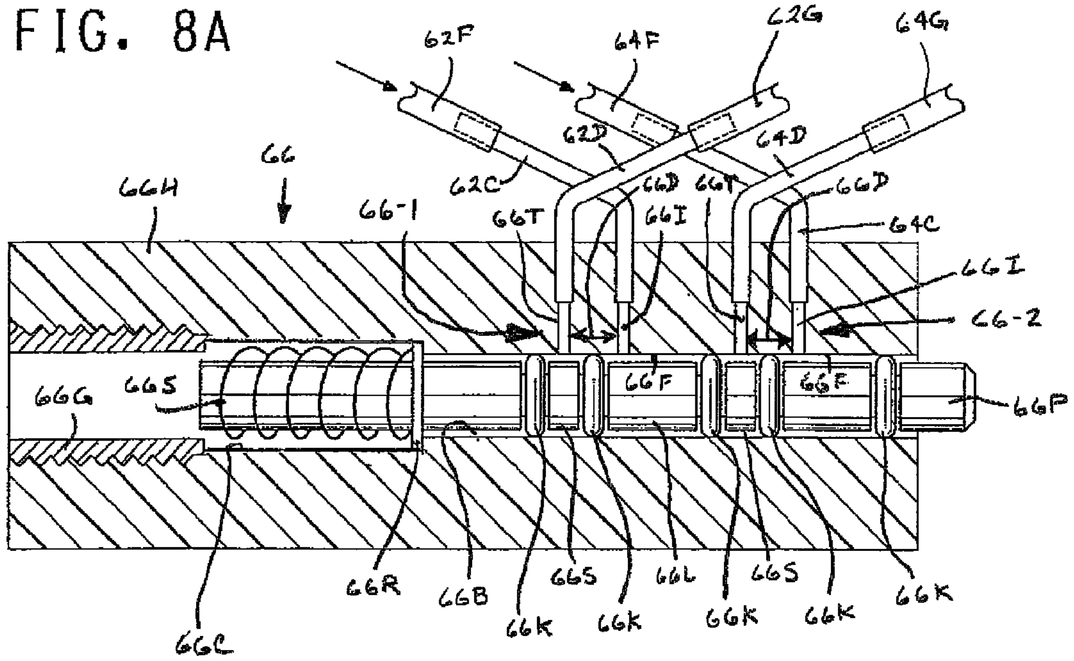
Figure 8B:
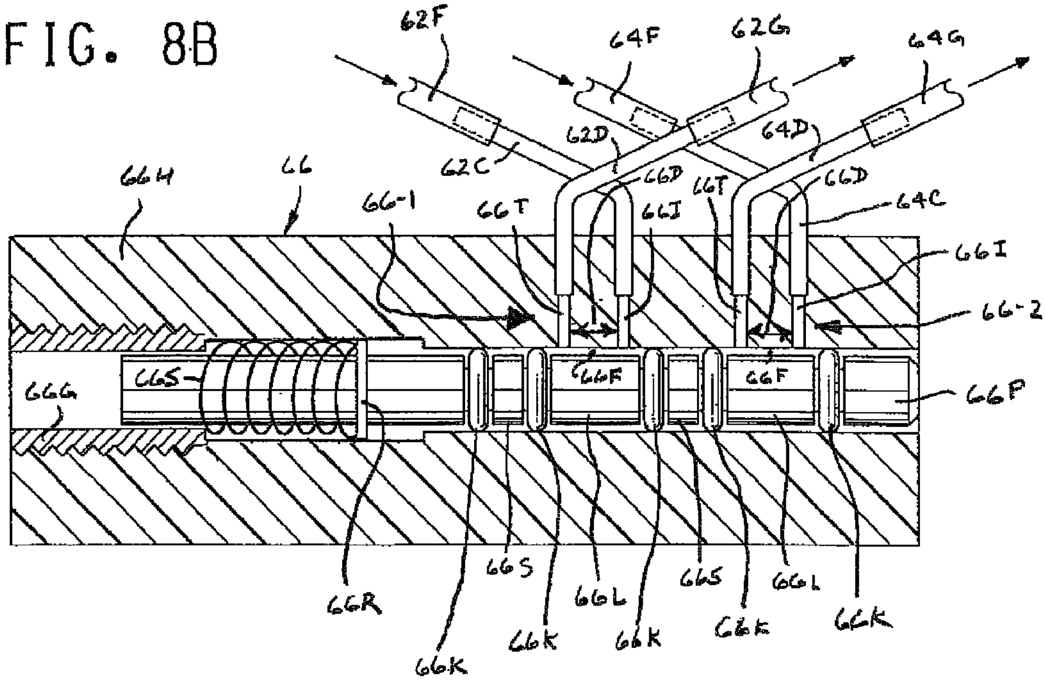
Figure 9:
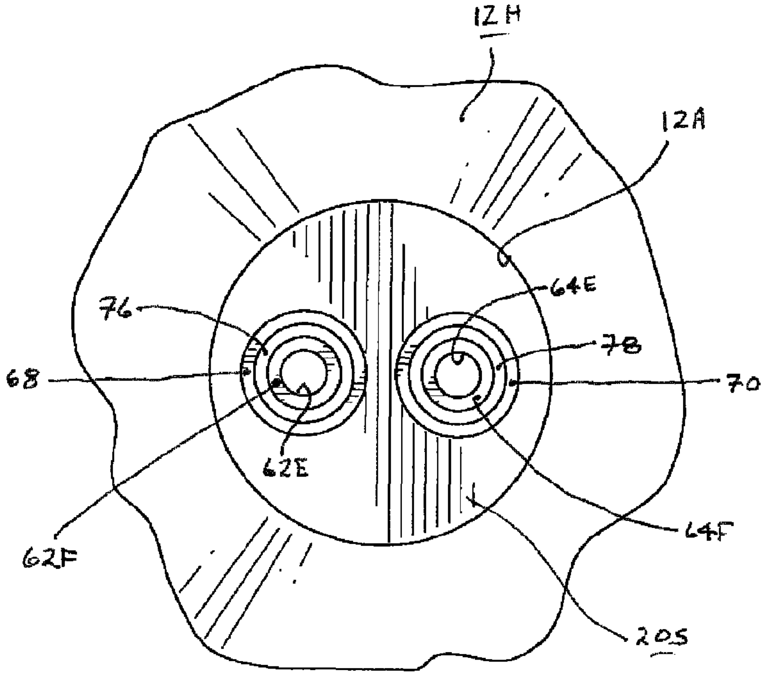
Figure 10A:
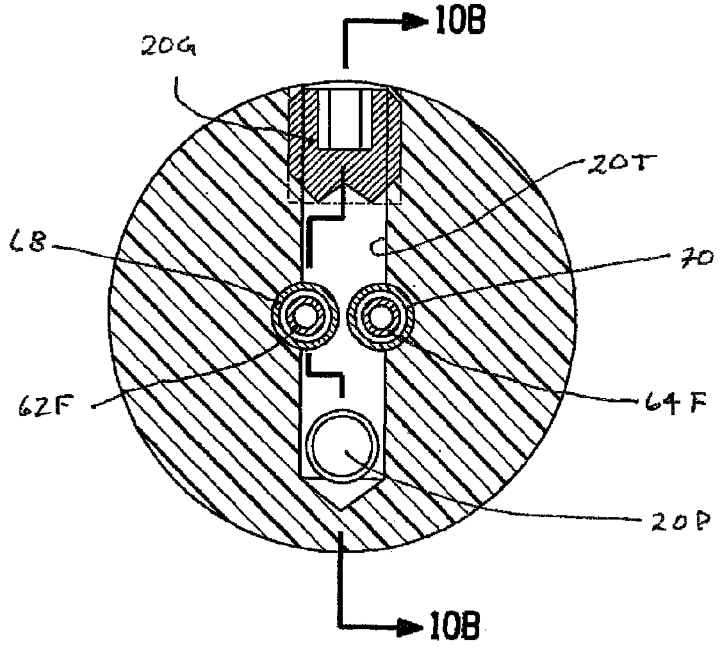
Figure 10B:
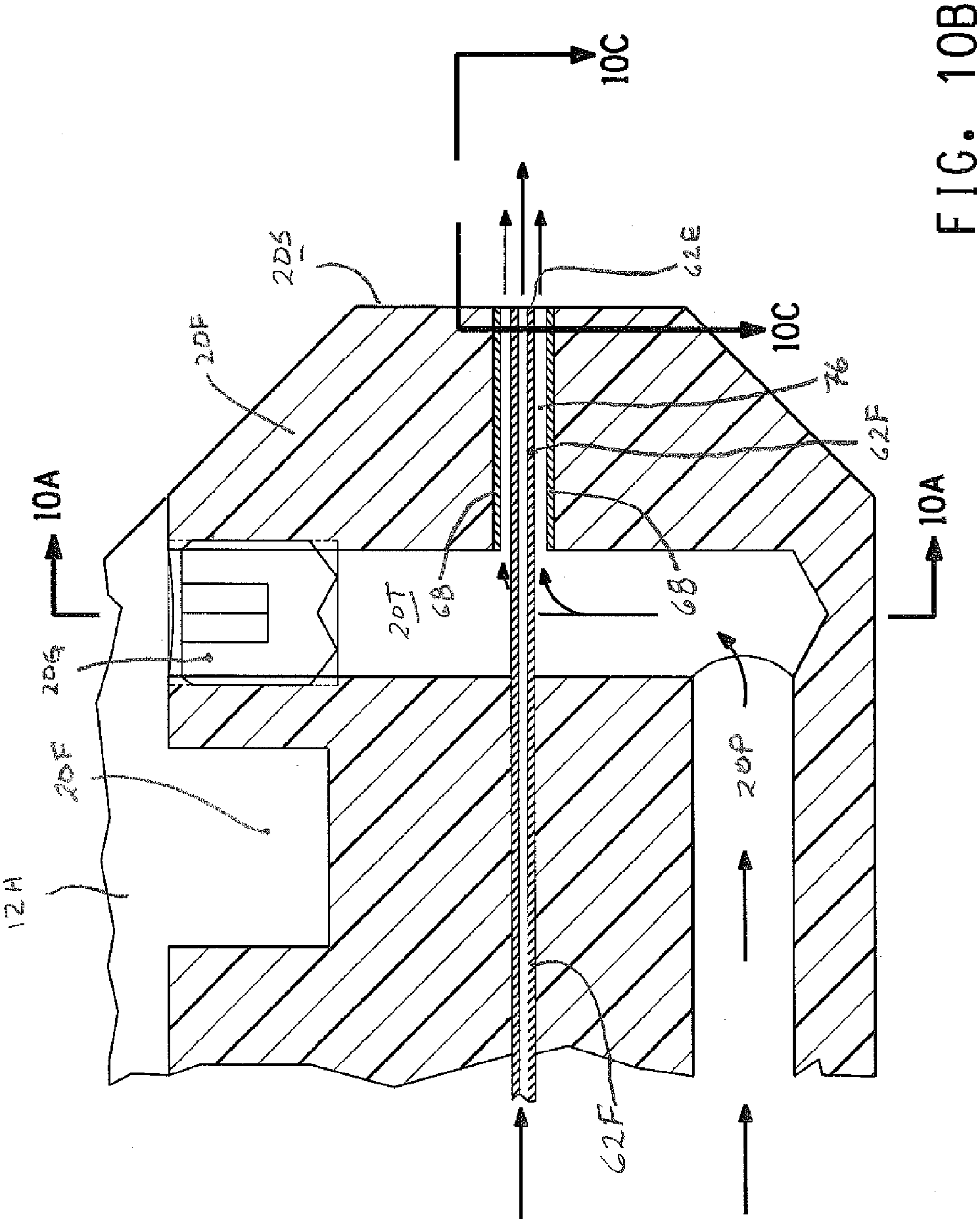
Figure 10C:
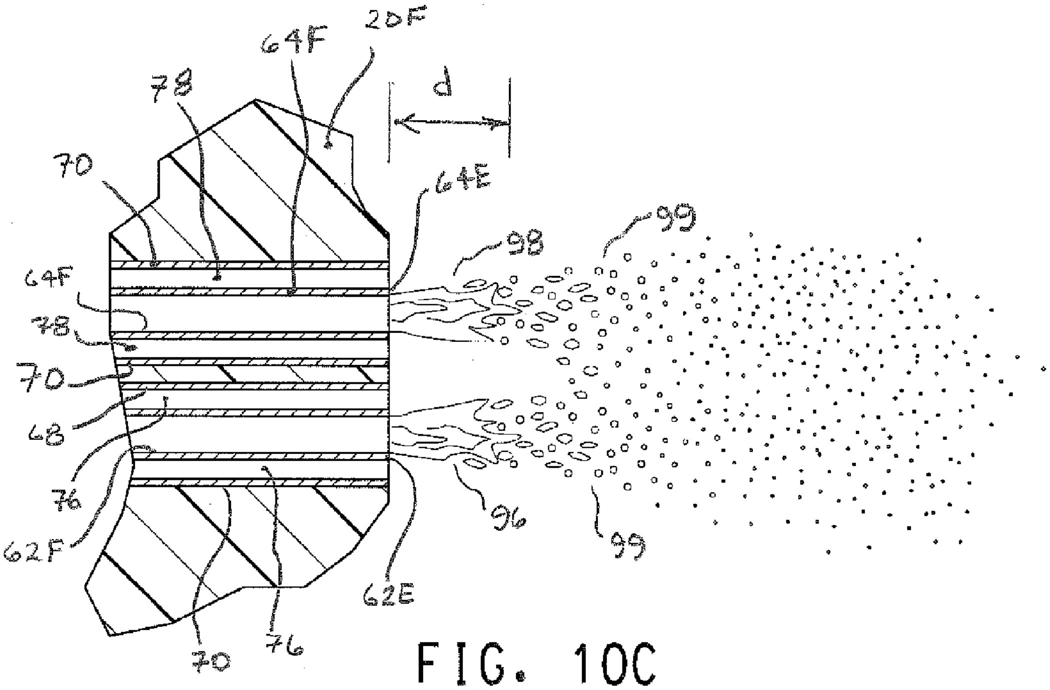
Figure 12:
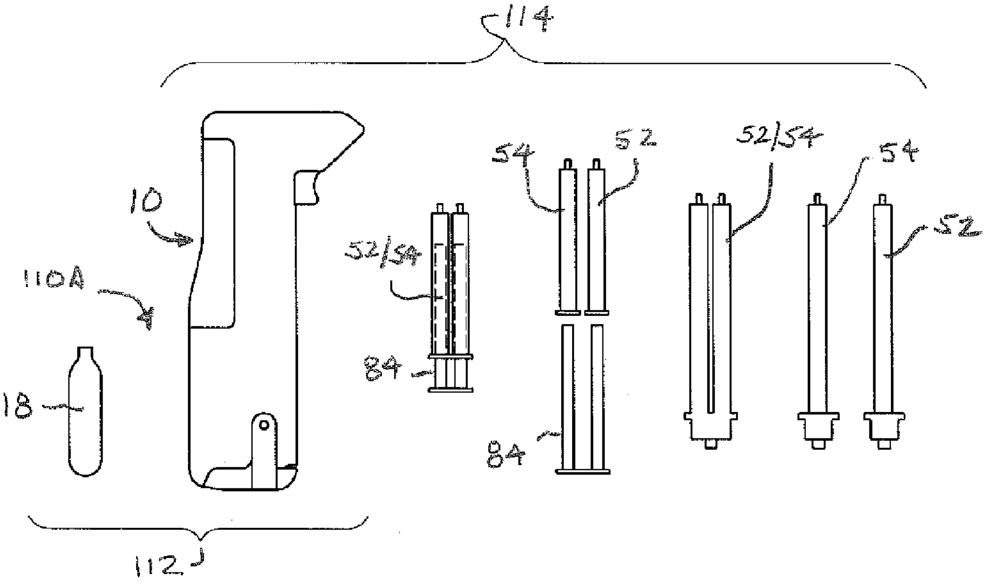
Figure 11C:
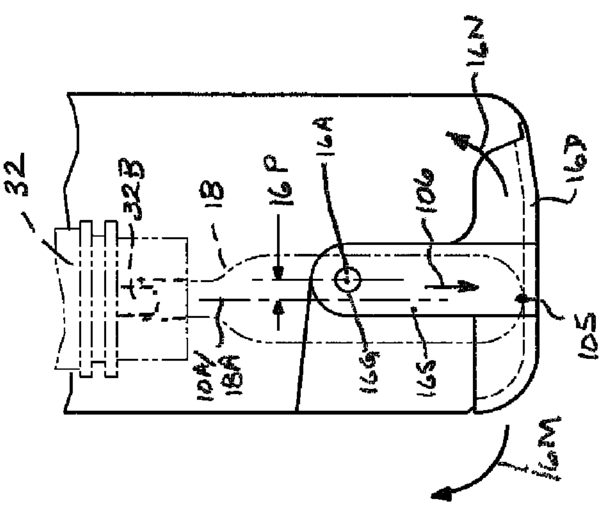
Figure 11B:
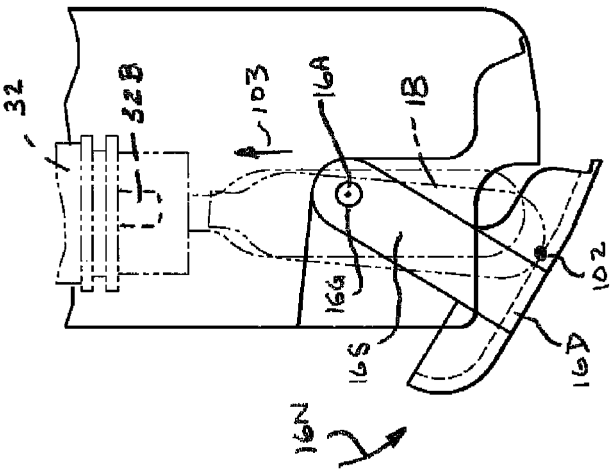
Figure 11A:
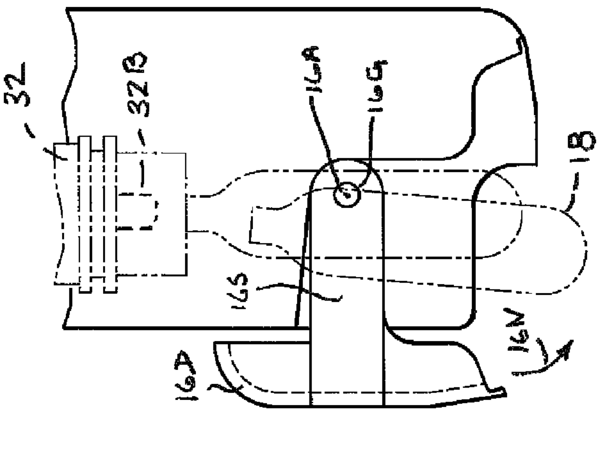

the views in FIGS. 7A and 7B showing the relative position of the trigger and flow interrupter while the trigger occupies its rest position and a first operational position, respectively, the view in FIG. 7C showing the relative position of the trigger and flow interrupter while the trigger occupies a second operational position;

FIG. 7D is a section view taken along section lines 7D-7D in FIGS. 4A and 5A illustrating the mounting of the operating trigger within the both shells of the housing;

FIG. 8A is an enlarged side section view of the position of the spool valve of the flow interrupter while the trigger occupies the rest and first operational positions shown in FIGS. 7A and 7B, respectively;

FIG. 8B is an enlarged side section view similar to FIG. 8A illustrating the position of the spool valve of the flow interrupter while the trigger occupies the second operational position shown in FIG. 7C;

FIG. 9 is an elevation view taken along view lines 9-9 in FIGS. 4A and 5A illustrating the dual orifice outlet of the flow nozzle;

FIG. 10A is a section view taken along section lines 10A-10A in FIGS. 4A, 5A and 10B illustrating the structure of the dual orifice flow nozzle in the direction of liquid and gas flows;

FIG. 10B is a section view taken along section lines 10B-10B in FIG. 10A;

FIG. 10C is a section view taken along section lines 10C-10C in FIG. 10B illustrating the exit of two discrete liquid streams from the ends of the liquid discharge lines and the aerosol and mixing action imposed on the liquid streams by the adjacent emanating gas streams;

FIGS. 11A, 11B and 11C are side elevation views diagrammatically illustrating the operation of the over-center cam mechanism lever action for the exterior closure that forms part of the cartridge support arrangement of the housing of the dispensing device; and FIG. 12 is a diagrammatic illustration of a various forms of a kit for dispensing a liquid material, the kit including a self-contained, hand-held dispensing device in accordance with the present invention together with one or more liquid container(s) and/or a cartridge holding a pressurized fluid.

DETAILED DESCRIPTION OF THE INVENTION

Throughout the following detailed description similar reference numerals refer to similar elements in all Figures of the drawings. It should be understood that various details of the structure and operation of the present invention as shown in various Figures have been stylized in form, with some portions enlarged or exaggerated, all for convenience of illustration and ease of understanding.

Figure 3:
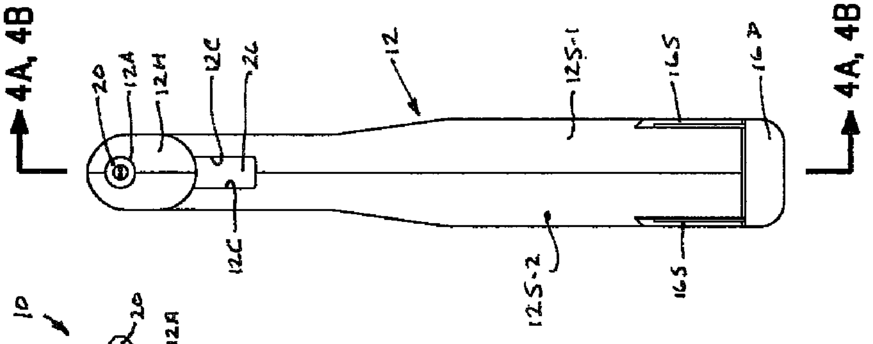
FIG. 3 is a front elevation view of the hand-held spray dispensing device shown in FIG. 1.
Figure 2:
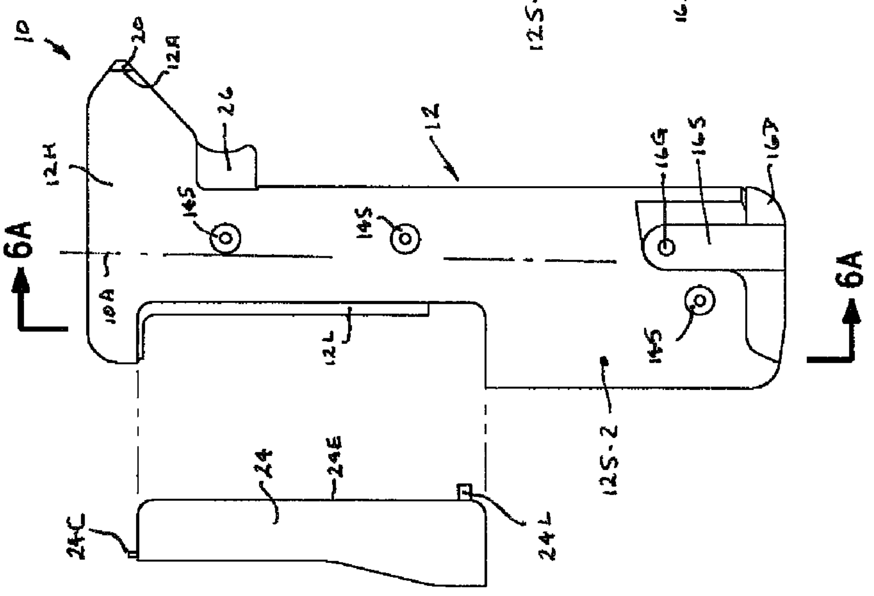
FIG. 2 is a side elevation view of the hand-held spray dispensing device shown in FIG. 1 with the back cover removed from the housing.
Figure 1:
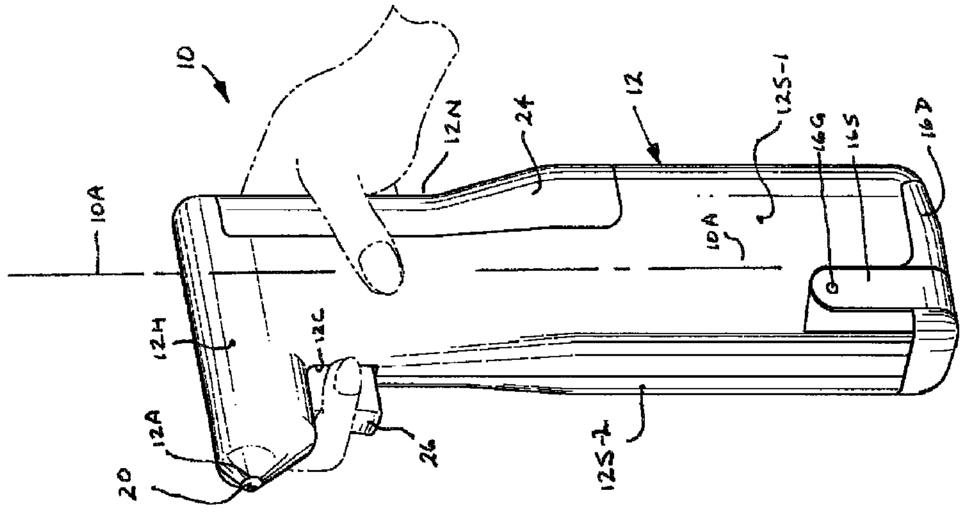
FIG. 1 is a perspective view of a self-contained, hand-held dispensing device in accordance with the present invention for dispensing an aerosol spray containing a mixture of a first and a second liquid component over a predetermined site.

FIG. 1 shows a perspective view of the exterior of a self-contained hand-held spray dispensing device ("sprayer") generally indicated by the reference character 10 in accordance with the present invention. By "self-contained" it is meant that all of the necessary components for dispensation of a liquid or mixture of liquids are contained in the device itself, without the need for any tethered connection, such as a connection to a source of pressurized fluid. FIGS. 2 and 3 are respective side and front elevations of the sprayer 10 of FIG. 1. The sprayer 10 has an axis 10A extending vertically therethrough.

The sprayer 10 is operative to dispense an aerosolized spray of one or two liquid material(s) over a predetermined site. Any liquid material, such as sterile water, disinfectant(s) and/or antibiotic(s), may be delivered to a site. The liquid materials may be the same or different from each other. The sprayer 10 is also able to dispense relatively higher viscosity liquids as a well-mixed aerosolized spray. The sprayer 10 is thus believed particularly useful to dispense different first and second liquid components of a two-part adhesive. These liquids adhesive components may have viscosities ranging from about ten to one thousand centipoise. The sprayer is capable of covering areas as small as about 2.5 $cm^2$ to relatively larger areas about four hundred (400 $cm^2$) or more.

The sprayer 10 includes a generally hollow housing 12 formed from first and second conjoined side shells 12S-1, 12S-2 that meet each other along a substantially planar joinder plane. The shells cooperate to define an elongated body with rounded front and rear edges. As will be described various structural features are integrally formed in complementary positions on the confronting interior surfaces of the shells. Thus, when the shells are conjoined these complementary structural features cooperate to securely support the various functional elements of the sprayer 10. The shells 12S-1, 12S-2 are conveniently held together by screws 14S (FIG. 2) that extend through openings 14A (FIGS. 4C, 4D) provided in one shell 12S-2. The screws 14S are preferably made from stainless steel and are threadedly received by various attachment features (indicated by the character 14F, FIGS. 4A, 4B) formed on the inside surface of the other shell 12S-1.

Figure 4B:
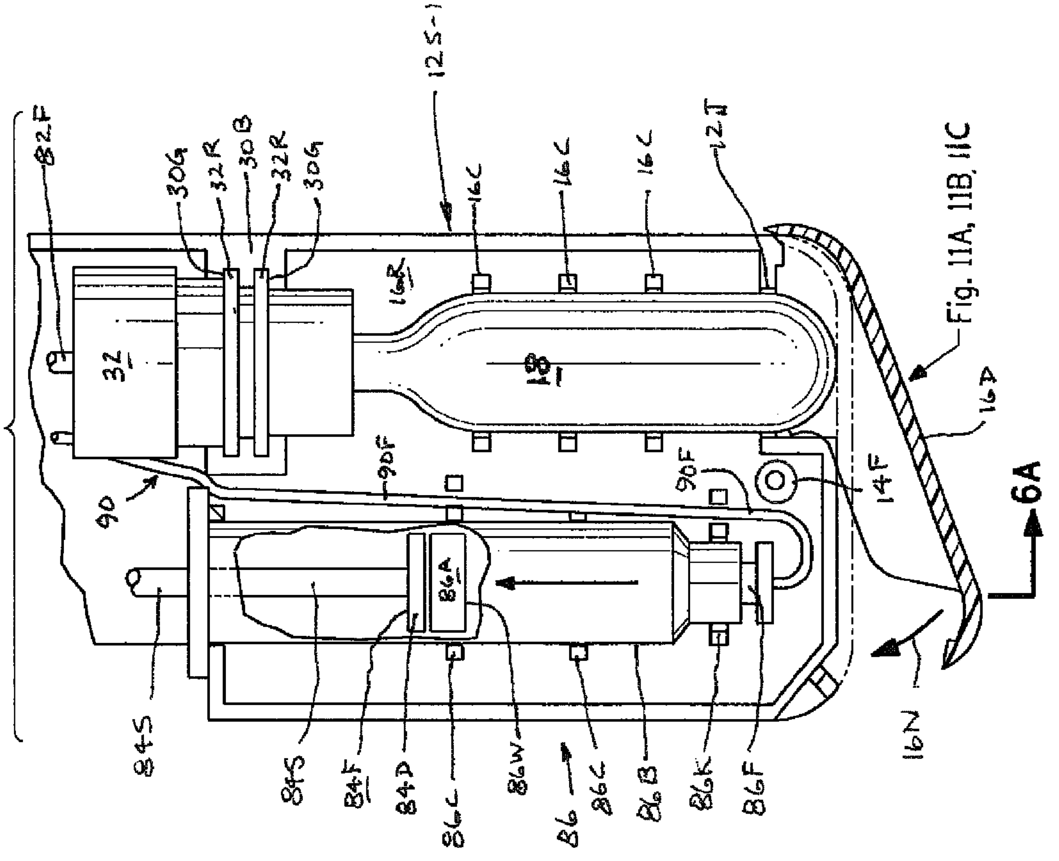

Referring to FIGS. 4B/4D and 5B, the peripheral edges at the lower ends of the shells 12S-1, 12S-2 are bent and form inwardly directed flanges that cooperate to define an interior floor 12F. The floor 12F partially closes the bottom of the hollow interior of the housing 12, leaving an access opening 12J that affords access to a compartmentalized region 16R on the interior of the housing. A cartridge support arrangement generally indicated by the reference character 16 is disposed in the compartmentalized region 16R. As will be developed the cartridge support arrangement 16 is able to receive and to support on the interior of the housing a cartridge 18 holding a pressurized fluid.

As illustrated in FIGS. 1 to 3 and 11A to 11C, the exterior lower end of the housing 12 is closed by a door 16D that comprises part of the cartridge support arrangement 16. The door 16D has a pair of straps 16S, each of which is connected to a respective one of the side shells 12S-1, 12S-2 through a stainless steel hinge pin 16G. The pins 16G are held by trunnions 16T (e.g., FIG. 4D) formed on the interior surfaces of the shells. The trunnion on the interior of the shell 12S-1 (FIG. 4B) is obscured by the cartridge 18. The door 16D is thus mounted for swinging movement in opposed opening direction 16M and closing direction 16N from a closed position (e.g., FIGS. 1-3, 11C) to an open position (e.g., FIGS. 4A, 4B, 11A, 11B), respectively.

As is best seen in FIGS. 11A through 11C the door 16D swings about an axis 16A that is oriented perpendicular to the joinder plane of the shells. Thus, the reciprocal swinging motions 16M, 16N of the door 16D occur in a plane that is parallel to the joinder plane of the shells. The swing axis 16A is offset from the axis 10A of the sprayer 10 toward the closing direction 16N (i.e., toward the closed door position, FIG. 11C) by a predetermined offset distance 16P. This relationship between the swing axis 16A and the axis 10A of the sprayer imparts desirable leverage actions, as will be discussed.

Referring again to FIGS. 1 through 3, at its opposite end the housing 12 narrows through a tapered neck region 12N leading to an elongated discharge head 12H. The discharge head 12H is oriented substantially perpendicular to the axis 10A of the sprayer 10. The outlet end of a multi-orifice discharge nozzle 20 projects through an aperture 12A provided at the front end of the discharge head 12H (see also, FIG. 9).

A portion of the rear margin of each side shell 12S-1, 12S-2 (extending from the back of the head 12H through the nape of the neck 12N) is bent inwardly to form another pair of flanges. These flanges cooperate to define a planar platform 22P (FIGS. 4A, 5A) on the interior of the housing 12. One end of the platform 22P is indented to form a notch 22N. The platform 22P, together with a fitting 22F (FIG. 4A, 5A) secured on the interior of the housing adjacent to the forward end of the platform 22P, cooperate to a form a container support arrangement 22 to be described.

A lip 12L (FIG. 2) is formed on the exterior of the shells adjacent the inwardly bent flanges that form the platform 22P. The lip 12L accepts the lateral peripheral edges 24E of a curved back cover 24. A central tab 24C at the leading end of the cover 24 and two lateral tabs 24L at the back end of each side of the cover 24 engage into corresponding respective recesses 12R (FIGS. 4A, 4C) provided in the shells that receive the cover 24 in snapping engagement. When received on the housing 12 the cover 24 and the platform 22P cooperate to define a substantially enclosed chamber 22C wherein containers 52, (e.g., FIGS. 4A, 5A, 6A, 6B) carrying the liquid material(s) to be dispensed from the sprayer 10 are received.

Cut-outs 12C (FIG. 3) in the front edge of each of the side shells 12S-1, 12S-2 (immediately beneath the discharge head 12H) cooperate to define a guide opening through which a reciprocally mounted multi-position trigger 26 extends. The region of the housing 12 directly beneath the discharge head 12H and the exterior of the back cover 24 cooperate to form a pistol grip whereby the sprayer 10 can be conveniently grasped and operated single-handedly by an operator, as suggested in FIG. 1.

In the preferred instance the shells and various other parts of the housing are injection molded from a suitable plastic material, such as polycarbonate. However, it should be understood that the housing may be made from any other suitable material such as metal or any other injection moldable thermoplastic.

Figure 4D:
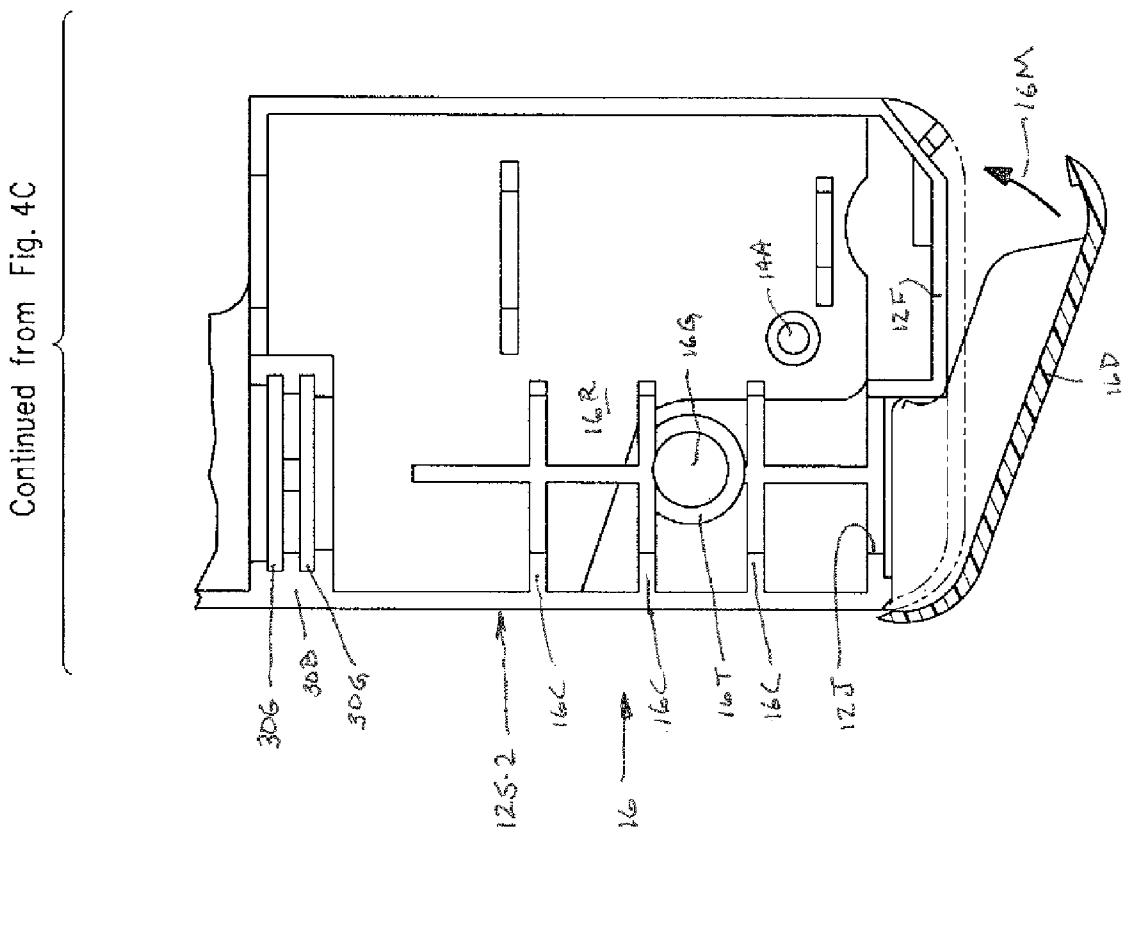

FIGS. 4A and 4B taken together show a composite elevation view of the interior surface of the shell 12S-1 as well as the disposition of various operational elements of the sprayer 10 supported thereby in accordance with a first embodiment of the present invention. FIGS. 4C and 4D taken together are a complementary composite elevation view of the interior of the shell 12S-2, with the paired FIGS. 4A/4B and 4C/4D oriented such that the shells 12S-1, 12S-2 are illustrated in booked relationship with each other.

Figure 5B:
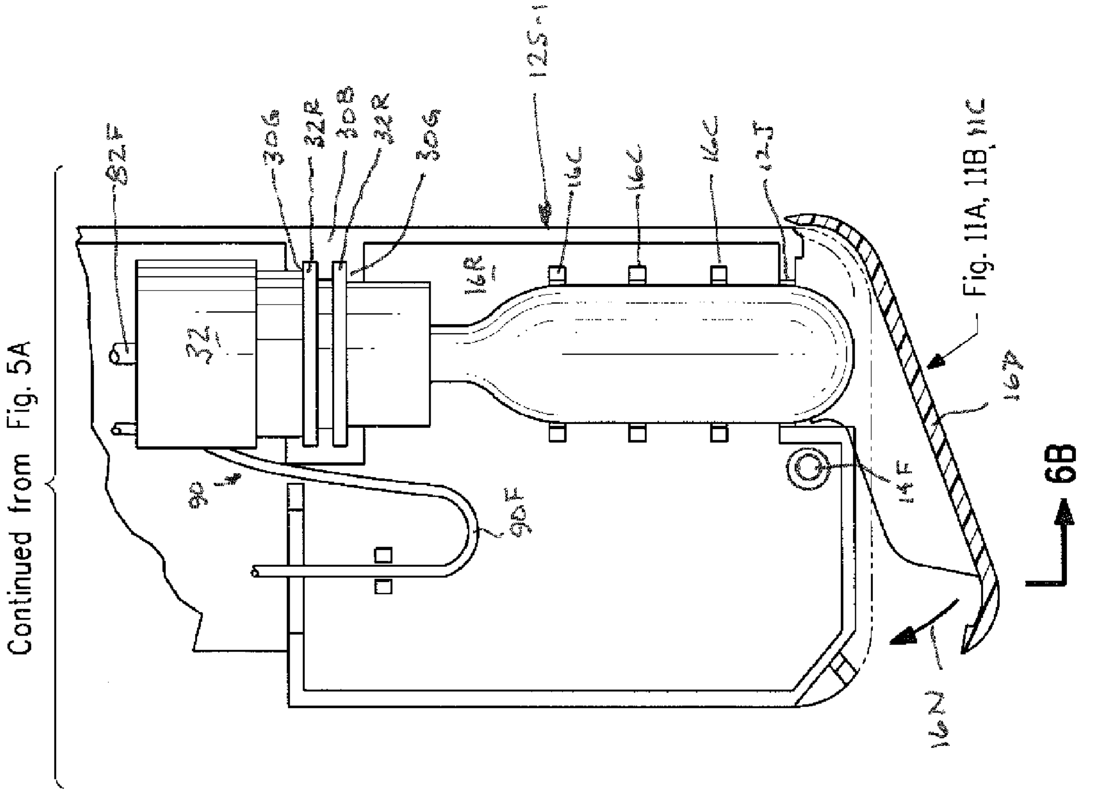

FIGS. 5A and 5B show a similar composite elevation view of the disposition of the various operational elements of the sprayer 10 on the interior surface of the shell 12S-1 in accordance with a second embodiment of the present invention. The shell 12S-2 shown in FIGS. 4C/4D may be used together with the shell 12S-1 of FIGS. 5A/5B to form the housing of the second embodiment of the sprayer 10. As will be developed, the primary difference between the embodiments of the invention discussed herein lies in the manner in which a pressurized fluid from a cartridge reservoir receivable in the housing is used to impart a motive force that ejects the liquid materials from their containers.

An array of semi-cylindrical cradles 16C (FIGS. 4B/4D and 5B) is integrally formed on the interior of the shells in the compartmentalized region 16R. The cradles 16C extend in spaced relationship inwardly into the housing from the access opening 12J. The cradles 16C cooperate with the door 16D to form the cartridge support arrangement 16 which is able to receive and support a pressurized fluid cartridge 18. The cartridge 18 defines a reservoir holding a charge of a pressurized fluid for the sprayer. The axis 18A of the cartridge 18 lies substantially collinear with the axis 10A of the sprayer (FIG. 11C).

The cartridge 18 is preferably implemented using a sixteen gram liquefied carbon dioxide bottle, having an initial internal pressure of eight hundred (800) psi available from Innovations In Cycling, Inc. Tucson, Ariz., as part number 2170. Carbon dioxide gas is the pressurized fluid of choice because of its compatibility with tissues of the human body. However, pressurized air, nitrogen or some other gaseous fluid may also be used as the motive fluid for the sprayer, if desired.

A semi-cylindrical boss 30B is integrally formed substantially midway along the interior of the shell 12S-1, 12S-2, above the cradles 16C. The inside surface of the boss 30B has spaced grooves 30G that accept annular ridges 32R formed on the exterior of a pressure regulator 32. The regulator acts as a pressure reducer to regulate the pressure of the gaseous fluid leaving the cartridge and entering the various pressurized fluid lines to be described. The inlet opening of the regulator has a tubular barb 32B (shown diagrammatically in FIGS. 11A through 11C) that punctures a metal seal formed over the mouth of the cartridge 18 and allows carbon dioxide gas to enter the regulator 32. A suitable regulator is available from Innovations In Cycling, Inc. Tucson, Ariz., as part number SA00196.

As perhaps best seen in FIG. 4A the outlet of the regulator 32 is connected by a flexible line 82F to the inlet port 38I of a flow control valve 38. The bottom surface of the valve 38 is supported on a bracket 38B formed on the shells. The valve 38 is secured in place by a metal pin that extends through an eyelet 38E provided on the valve casing. The ends of the pin are received in bosses 38S (e.g., FIG. 4C) provided on the interior surfaces of the shells. The valve 38 has an outlet port 38P and a vent port 38V. A suitable valve is available from Innovations In Cycling, Inc. Tucson, Ariz., as part number SA00195.

Lower and upper spaced partitions 42, 44 are provided on the interior of the shells 12S-1, 12S-2 above the region occupied by the valve 38 (see also, FIGS. 7A through 7D). The partitions 42, 44 extend into the interior of the housing from points adjacent to the trigger openings 12C. The actuating rod 38R of the valve 38 extends through an opening 42A formed in the lower partition 42.

Parallel guide tracks 46, 48 are disposed on the interior surfaces of the shells in the space between the partitions 42, 44. As best seen in FIGS. 7C and 7D the guide tracks 46, 48 on the interior of the shell 12S-1 each have an upstanding leg 46L, 48L that extends toward the corresponding track 46, 48 on the confronting interior surface of the other shell 12S-2. The leg 48L on the upper guide track 48 has an opening that also conveniently serves as one of the features 14F that accepts the screws 14S that hold the shells together.

The trigger 26 takes the form of a substantially rectanguloid body member having a front edge surface 26F that is contoured to receive the finger of an operator. An upper and a lower slot 26U, 26L extend in parallel through the rear half of the trigger body. Each of the upstanding guide legs 46L, 48L extends into a respective one of the slots 26U, 26L.

The guide tracks 46, 48 together with the lower and upper partitions 42, 44 cooperate to define an internal passageway for the trigger 26. The interposition of each leg 46L, 48L into its respective guide slot 26U, 26L serves to guide the trigger 26 as it reciprocates with respect to the housing 12 of the sprayer 10. The reciprocating motions of the trigger 26 are substantially perpendicular to the axis 10A of the sprayer 10. A biasing spring 26S captured in one of the slots 26U, 26L biases the trigger 26 to its forward, rest, position illustrated in FIGS. 4A, 5A and 7A. Depending upon the amount of biasing force desired a second spring may be captured in the other slot, if desired.

An actuating arm 26A projects from the upper edge surface of the trigger body. The arm 26A terminates in a rearwardly projecting finger 26F. The forward edge of the arm is undercut to define a notch 26N. An inward extension 12I on the head 12H registers into the notch 26N when the trigger 26 occupies its rest position and prevents the trigger 26 from being ejected from the housing 12 by the force of the biasing spring 26S. The lower edge surface of the trigger 26 has a detent recess 26D formed therein. The detent recess 26D is positioned to accept the tip of the actuating rod 38R of the valve 38 when the trigger 26 is in the rest position (e.g., FIG. 7A).

A first and a second liquid container 52, 54, each holding a liquid material to be dispensed by the sprayer 10, are receivable in side-by-side relationship on the support platform 22P located in the support chamber 22C. In both embodiments illustrated herein the containers 52, 54 are implemented using a unitized dual syringe structure such as that available from Med Mix Systems AG, Rotkreuz, Switzerland.

As noted earlier the sprayer 10 is preferably used to dispense a well-mixed aerosolized spray of different first and second liquid components of a two-part adhesive. Some of the components of such adhesives having viscosities in the range from about one centipoise to about one thousand centipoise or more, that is, a range of consistency from water (one centipoise) to castor oil. For example, an aqueous solution of a dextran aldehyde adhesive component has a viscosity in the range from about two to about two hundred (2-200) centipoise. An aqueous solution of a polyethylene glycol amine adhesive component (also known as "PEG amines") has a viscosity in the range from about ten to about three hundred (10-300) centipoise. Other adhesives that may be dispensed by a dispenser of the present invention include DuraSeal™ Dural Sealant System synthetic absorbable hydrogel available from Covidien; CoSeal® surgical sealant available from Baxter Healthcare; and Tisseel® fibrin sealant also available from Baxter Healthcare.

Figure 6A:
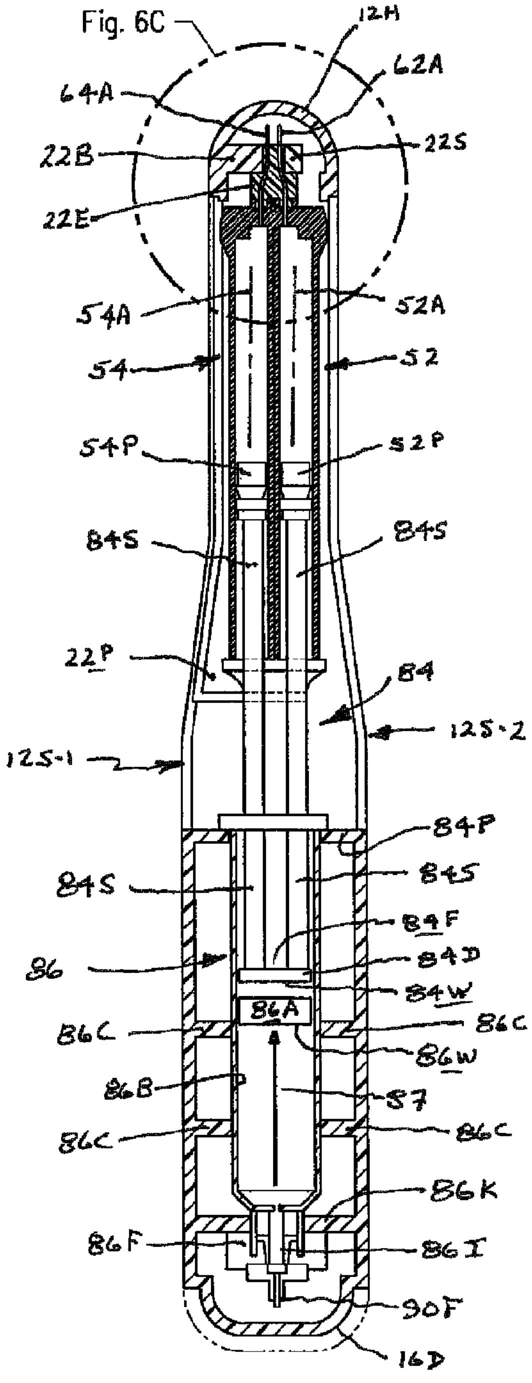
Figure 6B:
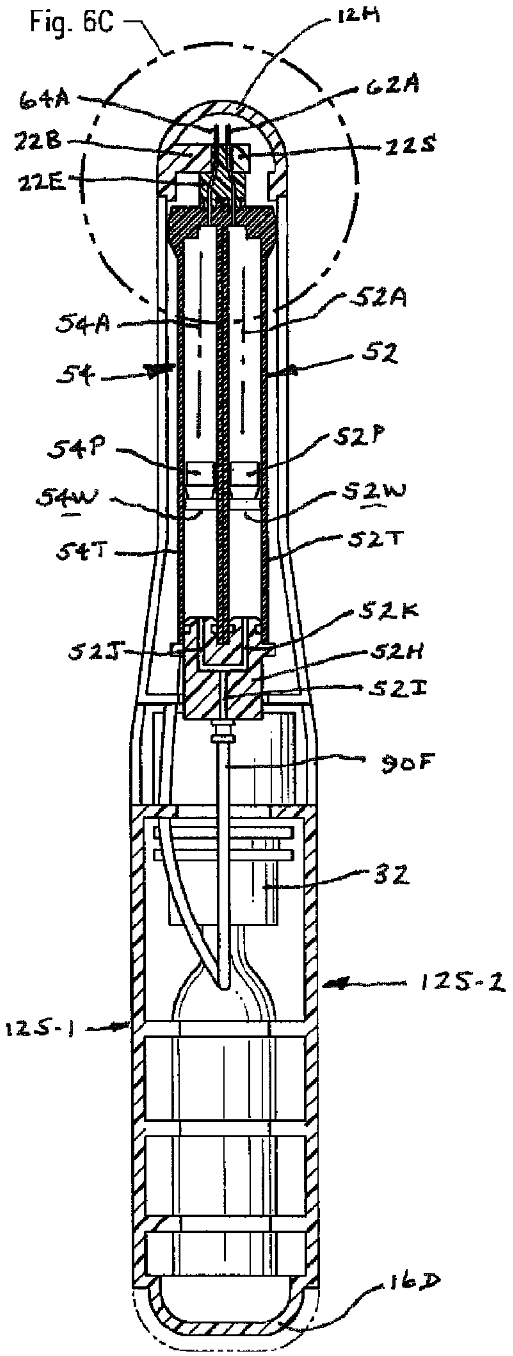
FIG. 6B is a top section view showing the hand-held spray dispensing device of FIGS. 5A and 5B taken along section lines 6B-6B therein.
Figure 6C:
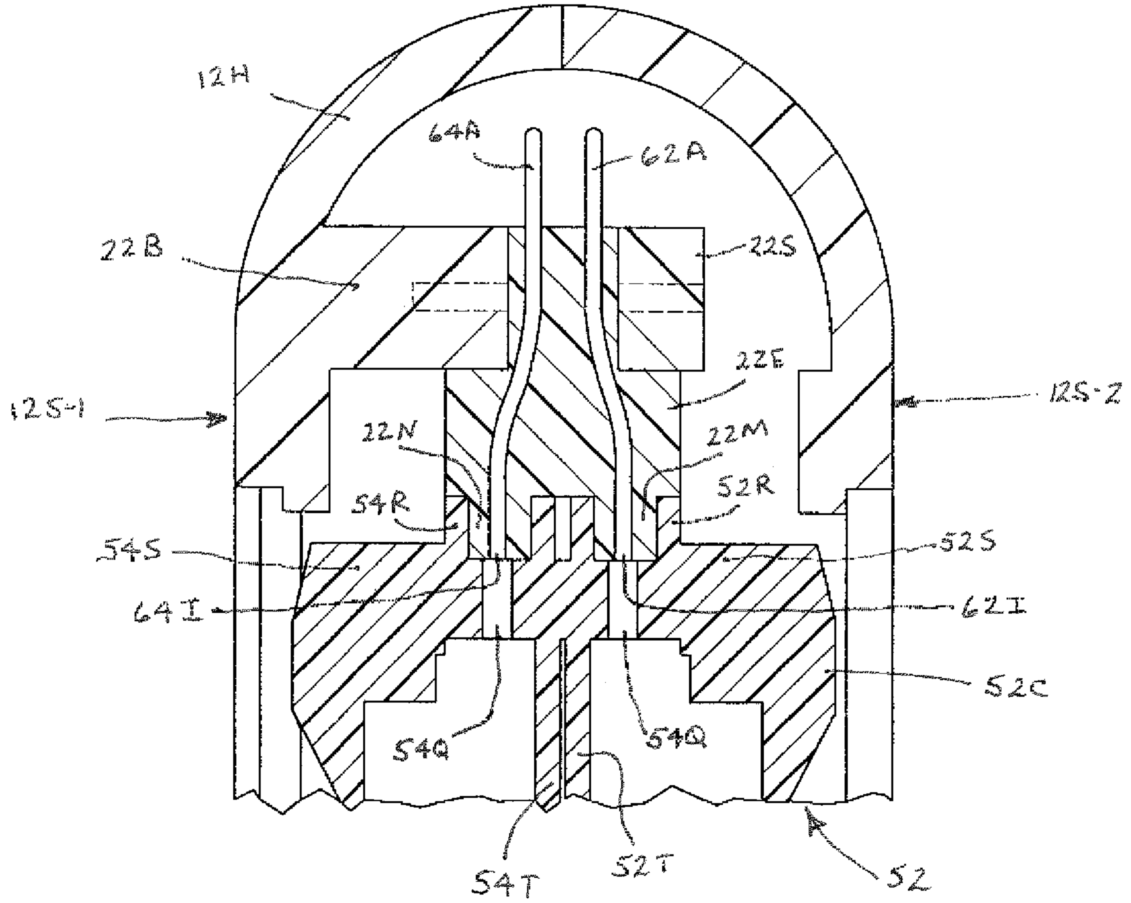
FIG. 6C is an enlarged section view of the circled portion of FIGS. 6A and 6B illustrating the structure at the discharge end of the liquid containers.

With particular reference to FIGS. 6A through 6C, each container 52, 54 includes a tubular barrel 52T, 54T. When supported on the container support arrangement 22 the respective axes 52A, 54A of each container extend parallel to the axis 10A of the sprayer 10. In the dual syringe arrangement illustrated the front end of each barrel 52T, 54T is closed by a portion 52S, 54S (FIG. 6C) of a unitary end cap 52C. The end cap 52C is integrally formed with the material forming the tubular barrels 52T, 54T. It should be understood that the use of separate containers for each liquid material, each container having a barrel and associated end cap through which a discharge port extends, lies within the contemplation of the invention.

Each portion 52S, 54S of the unitary end cap 52C has a discharge port 52Q, 54Q extending therethrough. Each discharge port 52Q, 54Q communicates with the interior of its associated barrel 52T, 54T and defines the opening through which liquid material is ejected from the container. The exterior surface of the end cap 52C has a pair of forwardly extending annular rims 52R, 54R. Each annular rim 52R, 54R surrounds a respective discharge port 52Q, 54Q.

The discharge ends of the containers 52, 54 are connected to the support fitting 22E that is part of the container support arrangement 22. The fitting 22E is mounted in a boss 22B that is formed on the back of the discharge head 12H. The fitting 22E is secured in place by a strap 22S which is attached to the boss 22B by screws 22W (FIGS. 4A, 5A). A nipple 22M, 22N (FIG. 6C) projecting from the back surface of the fitting 22E extends into a respective one of the annular rims 52R, 54R on the surface of the end cap 52E of the dual container 52/54.

At their opposite ends the containers 52, 54 are provided with a pair of gripping wings 52G, 54G (FIGS. 4A, 5A). One of the wings (e.g., the wing 52G) is received by the notch 22N disposed at the end of the platform 22P. As best seen in FIG. 7D a scalloped rib 24R depends from the inside surface of the back cover 24. When the cover 24 is received on the housing 12 and encloses the chamber 22C the edge of the rib 24R bears against the surfaces of the barrels 52T, 54T to maintain the containers in place against the platform 22P.

Referring again to FIGS. 6A, 6B each container 52, 54 has a liquid ejecting element operatively associated therewith. In the preferred instance the liquid ejecting element takes the form of an internal piston 52P, 54P that is slidably movable in sealed relationship with respect to the interior of the barrel 52T, 54T. In a manner to be described for each embodiment of the present invention each liquid ejecting element (e.g., each piston 52P, 54P) responds to a motive force imposed thereon to displace within its respective container to cause the material in the container to be expelled through its discharge port 52Q, 54Q.

The discharge port 52Q, 54Q of each container is connected to a liquid discharge line generally indicated by the reference character 62, 64, respectively (e.g., FIGS. 4A, 5A). Each discharge line 62, 64 extends through the interior of the discharge head 12H of the housing from an inlet end 621, 641 (FIG. 6C) beginning adjacent to the discharge port 52Q, 54Q of a container 52, 54 to an outlet end 62E, 64E (e.g., FIGS. 7A, 10C) located at the forward tip 20F of the nozzle 20. A flow interrupter 66 (best seen in FIGS. 7A through 7C, 8A, 8B) is interposed in each discharge line 62, 64 for controlling the passage of liquid therethrough.

The flow interrupter 66 is supported on the upper partition 44 and is there held in place by a bracket 66B extending from the inside surface of the discharge head 12H. The flow interrupter 66 may take the form of a spool valve having two valving stations 66-1, 66-2 (FIGS. 8A, 8B) although any suitable flow control device may be used. A liquid inlet port 661 and a liquid outlet port 66T at each valve station 66-1, 66-2 extend through the valve housing 66H into fluid communication with the valve bore 66B. The housing 66H is preferably made from a polysulfone thermoplastic material that is able to be steam autoclavable without losing its temperature properties. The inlet and outlet ports for each valve station are spaced apart a predetermined axial distance 66D.

The flow control element of the flow interrupter 66 is an elongated, generally cylindrical spool 66P. The spool 66P is reciprocally movable in the valve bore 66B that extends axially through the housing 66H. In the embodiments illustrated the valve spool 66P reciprocates in directions that are substantially perpendicular to the sprayer axis 10A. The valve spool 66P is made of stainless steel.

For each valve station 66-1, 66-2 the valve spool 66P has two lands 66L and 66S separated by adjacent grooves. Each of the grooves receives a sealing gasket 66K that bears in sealing engagement against the inside surface of the valve bore 66B.

The outside diameter of the lands 66L is less than the inside diameter of the valve bore 66B such that an annular flow space 66F is defined therebetween. In the implementation chosen the axial extent of the shorter land 66S is less than the spacing 66D between the ports, while the axial extent of the longer land 66L is greater than the spacing 66D therebetween.

An enlarged coaxial counterbore 66C is provided in the rearward end of the valve housing. A collar 66R attached to the valve spool 66P serves as a retainer for one end of a biasing spring 66S. The other end of the spring 66S is held by a plug 66G that is threaded into the counterbore 66C.

The valve spool 66P is movable against the bias of the spring 66S from a closed, flow interdicting position to a second, open, position. In the closed position the bias spring 66S urges the collar 66R into contact against the internal shoulder 66H formed by the difference in diameters between the valve bore and the counterbore. The length of the spool 66P is such that in the flow interdicting position the free end 66F of the valve spool 66P projects beyond the housing 66H toward the finger 26F on the trigger arm 26A.

When the spool 66P occupies the closed position (e.g., FIG. 8A) the gasket 66K between the lands is located between the inlet and outlet ports for each valve station, thereby isolating these ports from each other and preventing flow therebetween. However, when the spool 66P is axially shifted to the open position (e.g., FIG. 8B) the inlet and outlet ports for each station are in fluid communication with each other, through the annular space 66F defined around the longer land.

The structure of the outlet nozzle is illustrated in FIGS. 9, 10A through 10C. The nozzle 20 has a generally cylindrical body portion terminating in a forward frustoconical tip portion. The frustoconical tip portion projects through the aperture 12A at the discharge end of the head 12H. The tip has a flat end surface 20S thereon. The nozzle 20 is secured in place by a retainer bracket 20R that circumferentially engages against the exterior of the nozzle. A finger 20F extending into a peripheral notch 20N on the nozzle 20 prevents the nozzle 20 from being ejected from the head 12H when the sprayer is in use. The nozzle is made from the same polysulfone material as the housing 66H.

A pair of hollow stainless steel sleeves 68, 70 extends axially into the nozzle 20 from the flattened end surface 20S. The sleeves 68, 70 terminate in fluid communication with a transversely extending passage 20T that is itself connected to a fluid supply passage 20P. After the passage 20T is machined into the nozzle the transverse passage 20T is closed by a plug 20G (FIGS. 10A, 10B).

Two stainless steel tubes 62F, 64F extend axially through the entire length of the nozzle 20. The tubes are potted in place. In the forward frustoconical tip portion of the nozzle 20 the tubes 62F, 64F extend coaxially through a respective sleeve 68, 70. The tubes 62F, 64F terminate at the flat surface 20S of the nozzle. The inside surface of each sleeve 68, 70 and the outside surface of a respective tube 62F, 64F cooperate to define annular flow spaces 76, 78 extending through the forward portion of the nozzle. The annular flow spaces 76, 78 have a predetermined flow area defined in a plane perpendicular to the axes of the tubes 62F, 64F and to the axes of the respective concentric sleeves 68, 70. The sleeves 68, 70 may be omitted, in which case the tubes 62F, 64F extend through bore formed in the nozzle.

In the embodiments illustrated each respective liquid discharge line 62, 64 is implemented by interconnected lengths of rigid and flexible tubing.

The initial section of each discharge line 62, 64 is defined by a substantially ninety degree bent length of metal tubing 62A, 64A (FIG. 6C) that extends through the fitting 22F. The final section of each discharge line is realized by the stainless steel tubes 62F, 64F that extend through the nozzle 20 (FIG. 10C). A first central section 62C, 64C and a second central section 62D, 64D (FIGS. 8A, 8B) of each discharge line 62, 64 are respectively connected to the inlet port and the outlet port at each valve station 66-1, 66-2. These central sections 62C, 62D, 64C and 64D are also implemented with bent stubs of stainless steel tubing. A first length 62F, 64F (FIGS. 7A, 7B) of flexible tubing (connecting the end of the initial tubing sections with the valve inlet stub) and a second length 62G, 64G of flexible tubing (connecting the valve outlet stub to the final tubing section) complete the discharge lines 62, 64.

A pressurized fluid supply line 82 connects the pressurized fluid reservoir (i.e., the cartridge 18) receivable by the cartridge support arrangement 16 into fluid communication with the outlet end of each liquid discharge line. The pressurized fluid supply line 82 includes (FIGS. 7A, 7B):

- the length 82F of flexible tubing disposed between the regulated output of the cartridge 18 (from the regulator 32) and the valve 38;
- a length 82L of flexible tubing connecting the valve outlet 38P to the fluid supply passage 20P at the nozzle 20;
- the fluid supply passage 20P and interconnecting transverse passage 20T formed in the nozzle; and
- the two hollow stainless steel sleeves 68, 70 branching from the transverse passage 20T.

The valve 38 controls the flow of pressurized fluid through the pressurized fluid supply line 82.

In accordance with the first embodiment of the invention the pistons 52P, 54P in the barrel of each respective container 52, 54 are connected to a common force transmitting yoke arrangement 84 (FIG. 6A). In the implementation of the first embodiment of the invention the yoke 84 includes a pair of rearwardly extending shafts 84S that are connectable to the rear surface of a respective piston 52P, 54P. Each shaft 84S projects through the open back end of the barrel in which the piston is received. Each shaft 84S may be cruciform in a plane perpendicular to its axis whereby the shaft 84S may be centered with respect to the barrel in which it is received. Each piston shaft 84S is, in turn, connected to a first surface 84F of an actuating disc 84D. The opposite side of the actuating disc 84D defines a force-receiving working surface 84W against which an actuating force may be applied.

The actuating disc 84D of the yoke 84 is itself able to be received within and reciprocally movable with respect to an actuator 86. The actuator 86 extends though an opening provided in a support partition 86P located just rearwardly of the support platform 22P. The actuator 86 is supported along its length by an array of cradles 86C. The actuator 86 includes a cylinder 86B the inlet end of which is closed by a fitting 86F. A fluid inlet passage 861 extends through the fitting 86F. The actuator 86 is securely affixed to the interior surface of the shells by a clamp 86K.

A movable abutment, or plunger, 86A is disposed in slidable sealed relationship with respect to the interior of the actuating cylinder 86B. The surface 86W of the plunger 86A presented to the fitting 86F defines a working surface against which a pressurized fluid introduced into the interior of the cylinder 86B through the fluid inlet 861 passage may act (in the direction 87). The opposite surface of the plunger 86A defines a force transmitting surface that is engagable in force transmitting contact with the working surface 84W of the disc 84D receivable in the cylinder 86B. It should be appreciated that in an alternative implementation the plunger 86A may be integrated with the disc 84D. In that event the working surface exposed to pressurized fluid is carried on the actuating disc 84D itself and constitutes the working surface of the disc.

Another pressurized fluid supply line generally indicated by reference character 90 (branching from the outlet port 38P of the valve 38) connects the pressurized fluid reservoir (i.e., the cartridge 18) into fluid communication with the working surface 84W of the yoke 84. This pressurized fluid supply line also includes the length 82F of flexible tubing disposed between the regulator and the valve, as well as a length 90F of flexible tubing connecting the valve outlet 38P to the inlet passage 861 formed in the fitting 86F. The valve 38 also controls the flow of pressurized fluid through this pressurized fluid supply line.

FIGS. 5A, 5B, 6B illustrate an alternative embodiment of the invention. In this embodiment the rear surface of the liquid ejecting element (e.g., each piston 52P, 54P) defines the working surface 52W, 54W against which a pressurized fluid flow is directed thereby to generate the motive force to eject liquid from the containers 52, 54. Accordingly, the rear of each barrel 52T, 54T is closed by an integrated end cap 52H having a fluid inlet passage 521. The inlet passage 521 bifurcates into respective channels 52J, 52K that are in fluid communication with the interior of each barrel. The force transmitting yoke and the actuator cylinder of the first embodiment may thus be omitted.

As seen from FIG. 6B the pressurized fluid supply line 90 from the cartridge reservoir is connected to the end cap 52H and, through the bifurcated channels 52J, 52K therein thus placed in direct fluid communication with the rear working surface of each piston. The valve 38 also controls the flow of pressurized fluid through this pressurized fluid supply line.

-o-0-o-

With the structure of a sprayer in accordance with both embodiments of the present invention having been fully described, the details of its operation may be set forth.

It is assumed for purposes of discussion that the sprayer 10 in accordance with either embodiment of the invention is loaded with at least one but more preferably a pair of containers 52, 54, one or both of which contain a liquid material. In a typical implementation a pre-filled five (5) ml dual syringe (available from Med Mix Systems AG) with a first liquid bioadhesive component in one barrel and a second liquid bioadhesive component in the other barrel are received by the container support arrangement 22.

Any of the other adhesives mentioned above may also be used. Moreover, the device could also be used to spray single component liquids such as sterile water for irrigation, disinfectants or antibiotics. Single component spraying can be done by filling both barrels with the same liquid material or by providing a single syringe design.

The preferred ratio of the volume of material in the first container to the ratio of the volume of material in the second container is about 1:1. However, the ratio of the volume of material in the first container to the ratio of the volume of material in the second container may lie within a range from about 1:1 to about 1:10; more particularly in the range from about 1:4 to about 1:10; and even more particularly in the range from about 1:7 to about 1:10.

It is also assumed that a gas cartridge 18 is inserted in the cartridge support arrangement 16.

In this disposition the discharge ends of the containers 52, 54 are supported by the fitting 22E such that the discharge port 52Q, 54Q of each container is in fluid communication with the inlet end 621, 641 of its respective liquid discharge line 62, 64. The containers may be individual or dual containers of either type already discussed.

As seen in FIG. 6A, if the type of container using the force transmitting yoke 84 is being employed the actuating disc 84D of the yoke is inserted into the actuating cylinder 86B. In this event the line 90F is connected to the fitting 86F at the inlet end of the actuator 86. FIG. 6B illustrates the connections if containers of the alternative type are employed, wherein the line 90F is connected to the fitting 52H at the inlet end of the containers 52, 54.

The sequence of operations involved in loading of the cartridge 18 into the cartridge support arrangement 16 are illustrated in FIGS. 11A through 11C. At the time of use, the operator opens the hinged door 16D communicating with the cartridge compartment 16R and inserts the cartridge 18 thereinto through the access opening 12J (FIG. 11A). As noted earlier the door 16D is implemented in the form of an over-center cam mechanism such that, as the door 16D is moved toward the closed position (in the direction 16N) the interior of the door 16D strikes against the protruding end of the cartridge (FIG. 11B). This interaction is illustrated by reference character 102 (FIG. 11B) and forces the mouth of the cartridge 18 in the direction 103 against the barb 32B. The barb 32B punctures the metal seal over the mouth of the cartridge 18 as the cartridge seats thereon. Puncturing of the seal allows fluid communication from the cartridge 18 into the regulator 32.

Once the cartridge 18 is received in the regulator 32 a further advantage attendant with the use of the over-center cam mechanism provides a fail-safe mechanism that prevents the cartridge from being removed from the dispenser. Recoil of the gas cartridge 18 from the regulator forces the cartridge into contact with a point 105 on the interior of the door 16. The point 105 lies on the axis 18A of the cartridge 18. This contact generates a reaction on the door 16D (in the direction 106) that levers the door toward the closed position (i.e., in the direction 16N). The door 16D is thus prevented from opening while the cartridge 18 contains gas. However, when the cartridge 18 is spent, the reaction force falls to zero, allowing the over-center hinge to be opened.

With one or both of the containers 52, 54 received in the container support arrangement 22 and with the cartridge reservoir 18 received in the cartridge support arrangement 16, the operator grasps the sprayer 10 with one hand using the pistol grip. The protruding tip of the nozzle 20 is pointed at a target tissue and the two stage trigger 26 is depressed by the index finger.

The trigger 26 responds by moving in the direction of the arrow 93 from a rest position shown in FIG. 7A to a first operational position shown in FIG. 7B.

This movement of the trigger 26 moves the detent recess 26D so that the lower edge surface of the trigger 26 depresses the operating rod 38R (in the direction 94, FIG. 7B). This action opens the valve 38, which permits simultaneous pressurized fluid flow from a cartridge:

(i) through the pressurized fluid line 90 into contact against a working surface; and (ii) through the pressurized fluid line 82 over the outlet ends 62E, 64E of the liquid discharge lines 62, 64.

The flow through the first pressurized fluid imposes a motive force on either the working surface 86W of the plunger 86A or directly onto the working surface defined on each piston. In either event the pistons 52P, 54P are displaced within the barrels 52T, 54T causing the liquid in the container 52, 54 to be ejected through the discharge port thereof and into the discharge lines. However, owing to the presence of the flow interrupter 66, liquid is prevented from flowing through the liquid discharge lines to the outlet ends.

The trigger 26 is sequentially movable from the first operational position (FIG. 7B) to a second operational position shown in FIG. 7C. As the trigger 26 moves to the second operational position (in the direction 95) the finger 26F on the trigger arm 26A bears against the end of the spool 66P of the flow interrupter 66. The spool 66P is thus displaced against the force of the spring 66S, opening both of the liquid discharge lines. This permits liquid flow through both valve stations 66-1, 66-2 of the flow interrupter 66, allowing the passage of liquid material through the liquid discharge lines.

As diagrammatically illustrated in FIG. 10C two segregated liquid streams 96, 98 exit from the discharge ends 62E, 64E of the respective discharge lines 62, 64. At a short distance "d" after leaving the surface 20F of the nozzle 20 the liquid streams 96, 98 are sheared by the pressurized fluid emanating from the sleeves 68, 70 that surround each discharge line. This shearing of the liquid streams 96, 98 creates droplets which form a spray (illustrated diagrammatically at reference character 99), and which allows the liquids to intermix as the streams transit toward the target tissue.

To halt liquid flow the steps are reversed. The trigger 26 is released and sequentially reverts toward the first operational position and then to the rest position. Owing to the two stage trigger operation described, aerosolizing flow through the nozzle 20 starts before and finishes after the passage of any liquid material through each liquid discharge line. Pressurized fluid drains from the actuator through the nozzle 20.

The streams 96, 98 are kept apart until after they exit the respective discharge lines, thus avoiding any problem of gelation. The continued gas flow will strip any liquid remaining at the end of the discharge lines and prevent clogging.

It is important to maintain a consistent flow rate of the liquids with respect to the flow rate of the carbon dioxide gas since the relative velocities of these fluids determine the liquid droplet size and thus the efficiency of mixing. Smaller droplets are more easily dispersed and have a higher surface area to mass ratio and thus create more efficient mixing. The droplet size decreases when the liquid velocity is decreased at constant gas velocities. The droplet size also decreases when the gas velocity is increased at a constant liquid velocity.

Accordingly, it is important that the first and second pressurized fluid lines are complementarily configured with respect to each other such that:

the pressure of any fluid flowing through the first pressurized fluid line is able to act on the actuating surface of a yoke receivable in the actuator or the working surface of a piston to impose a motive force on a piston sufficient to cause a liquid material to emanate at a predetermined rate from the outlet end of each liquid discharge line, and, simultaneously, the velocity of any fluid flowing through the second pressurized fluid line being able to act to aerosolize any liquid material emanating from the outlet ends of the discharge lines.

For a given area of the annular flow spaces 76, 78, this balance is achieved by first adjusting the fluid pressure at the outlet of the regulator 32 to aerosolize the liquids, and then adjusting the area of the working surface against which the pressurized fluid acts to generate the motive force on the pistons 52P, 54P.

Once the proper balance for a particular application is achieved, the liquid flow rates and the gas flow rates are maintained, thus insuring consistent liquid flow and efficient mixing of the liquid streams without reliance upon any particular action on the part of the operator.

As a specific example, a sprayer as described in FIGS. 4A, 4B and 6A was constructed with the following attributes. The flow area of each of the two annular flow spaces 76, 78 in the nozzle was $5.8\times10^{-4}$ in$^2$ (0.375 mm$^2$). A pressure in the range of fifteen to thirty psi (and preferably about twenty psi) was found necessary to aerosolize two liquid components having viscosities about 20 centipoise and 160 centipoise, respectively.

It was also necessary to determine empirically the area needed for the plunger 86A to generate a force sufficient to displace the pistons in the containers given the viscosities of the liquid components and frictional forces inherent in the system. These frictional forces include friction between the plunger 86A and actuating cylinder 86B, between the pistons 52P, 54P and their respective barrels 52T, 54T, and the friction between the liquids and gaseous fluids and their passages. This area was found to be 0.30 in$^2$ (196 mm$^2$).

The embodiment of the invention utilizing the force transmitting yoke 84 may be preferable in situations in which it is necessary to have a consistent ratio of liquid components, time after time, batch to batch and sprayer to sprayer, so that a consistent hydrogel is formed and with the expected adhesive properties produced.

Since each liquid material is stored separately in a container and expelled by the motion of a piston, if the distances moved by the pistons expelling the liquid components are the same, the ratio of the volumes of the components expelled will be equal to the ratio of the cross-sectional areas of the barrels. Thus, linking the various pistons through a yoke so that both pistons travel the same distance guarantees that the ratio of the components will be constant for any distance traveled by the yoke.

As noted earlier the liquid components may be dispensed in ratios other than 1:1. With the yoke embodiment if the liquid containers have different inside diameters and the liquid components are intended to be dispensed in non equal but proportional volumes such as 1:4 or 1:10 ratios, then the diameters of the containers need to be sized so that the cross-sectional areas have the same ratios.

For example if a 1:4 ratio is desired the diameter of the larger barrel must be twice the diameter of the smaller. As another example, if a 1:10 ratio is desired the diameter of the barrel containing the greater volume of liquid must be approximately 3.162 times as large as the diameter of the other barrel.

In some situations the embodiment of FIGS. 5A, 5B and 6B may be preferred because it eliminates the need for an actuating cylinder, disc and yoke, thus reducing the size of the dispensing device. This embodiment may find special utility if both liquid viscosities are equal, the volume-dispense ratios are 1:1, and the liquid containers have the same diameter.

In addition, this embodiment may also be used with liquids of different viscosities, volume ratios other than 1:1, and containers with different diameters if adjustable flow restrictors are added into the liquid discharge lines. These restrictors are adjusted to obtain the proper flow of liquids without the need to adjust the fluid pressures. Alternatively, this embodiment may be accomplished by having two individual lines, one going to each piston, with a regulator and valve added to the second line.

-o-0-o-

A sprayer 10 in accordance with either embodiment of the present invention may also be used in kit form. FIG. 12 shows some illustrative configurations of various kits generally indicated by the reference character prefix 110 that may be assembled that include a sprayer 10.

In one form a kit 110A (the components of which are grouped by a bracket 112) comprises a sprayer 10 together with a cartridge 18 able to be received by the cartridge support arrangement 16 of the sprayer. In this kit 110A the container support arrangement 22 of the sprayer 10 may or may not be preloaded with suitable liquid container(s).

An alternative form of kit 110B (the components of which are grouped by a bracket 114) comprises a sprayer 10 together with one or more containers of liquid materials. The containers may be implemented as dual containers 52/54 of the first type (in which each container includes a piston connectable to a force transmitting yoke 84, e.g., FIG. 6A) or dual containers 52/54 of the second type (in which the end of the container is closed by an end cap with a fluid passage therethrough and in which the working surfaces are defined by surfaces of the piston, e.g., FIG. 6B). If a yoke 84 is required it may be already connected to the pistons or may be included as a separate element. Alternatively, the kit may contain individual containers 52, 54 of either type. In the kit 110B a cartridge 18 may or may not be present on the cartridge support arrangement 16 of the sprayer.

It is believed that the most convenient configuration of a kit combines an unloaded sprayer (i.e., no container(s) or cartridge preloaded therein) together with a cartridge and container(s) carrying the appropriate liquid(s) for a given application.

Those skilled in the art, having the benefits of the teachings of the present invention as hereinabove set forth may effect numerous modifications thereto. It should be understood that such modifications lie within the contemplation of the present invention, as defined in the appended claims.

For example, in the embodiments of the invention illustrated and discussed the cartridge reservoir 18 served as the fluid source for both pressurized fluid lines 82 and 90, through the regulator 32 and the valve 38. It should be understood that a separate, dedicated fluid cartridge, regulator and/or valve may be used for each line. It is also noted that the first and second pressurized fluid lines 82 and 90 share the same length of flexible tubing extending between the cartridge and the regulator. Separate dedicated lengths of line may similarly be provided.

In the embodiment of the invention shown in FIGS. 4A, 4B, and 6A (using the force transmitting yoke) the liquid ejecting element takes the form of a piston disposed within each cylinder. It lies within the contemplation of the invention for the liquid ejecting element to take the form of a roller or a wiper connected to the end of the yoke 84 that acts externally on the container. The container should be deformable so that the force from the roller or wiper causes the container to collapse and thus pushes the liquid from the container. The container may be in the form of a plastic flexible bag or an elastomeric tube. The liquid ejecting elements may require bearings, bushings, supports and guides to achieve the proper motion for conforming the container.

In all embodiments of the invention illustrated and discussed, it should be further understood that the motive force for any liquid ejecting element may be provided by arrangements other than using gas pressure. Examples of such other arrangements include spring mechanisms and motors.

That is to say, in connection with the first embodiment, the pressurized fluid line 90F from the valve 38 to the actuator may be eliminated and an actuating element in the form of a spring is placed in the actuator cylinder 86B behind the plunger 86A. In use, the plunger 86A is depressed manually as the yoke 84 is inserted, and the pistons 52P, 54P of the liquid containers 52, 54 are connected to the shafts 84S of the yoke. The spring supplies motive force to the yoke to cause the pistons to eject liquid material from the containers.

In another implementation the actuator 86 may be implemented using an electric motor-powered linear drive.

In connection with the second embodiment, the pressurized fluid line 90F from the valve 38 may be eliminated. An actuating element in the form of a spring is placed behind the piston 52P, 54P of each container 52, 54. The springs supply motive force to the pistons to eject liquid material from the containers.

What is claimed is:

1. A self-contained, hand-held spray dispensing device for dispensing one or more liquid material(s), the dispensing device comprising:

a container having a discharge port for each material, each container having a liquid ejecting element associated therewith, each liquid ejecting element being connectable to a force transmitting yoke having a working surface thereon, each container being responsive to a force imposed by the liquid ejecting element thereby to cause a liquid material in that container to be ejected from the discharge port, a housing;

a first and a second liquid discharge line disposed within the housing, each liquid discharge line having an inlet end and an outlet end;

a container support arrangement able to receive and to support a first and a second liquid container within the housing such that the discharge port of each container is disposed in fluid communication with the inlet end of a liquid discharge line;

an actuator disposed within the housing, the actuator being operative to apply a motive force to a working surface of a yoke receivable within the actuator;

a cartridge support arrangement disposed within the housing, the cartridge support arrangement being able to receive and to support a cartridge holding a pressurized fluid;

a first pressurized fluid line able to convey a pressurized fluid from a cartridge receivable within the housing into the actuator;

a valve able to control the flow of a pressurized motive fluid through the pressurized fluid line; and a trigger operatively associated with the valve, the trigger being movable from a rest position to a first operational position, when in the first operational position the trigger being operative to open the valve to permit a pressurized motive fluid from a cartridge receivable within the housing to flow through the pressurized fluid line into the actuator to generate a motive force on the working surface of a yoke receivable within the actuator, thereby to cause each liquid ejecting element to eject a liquid in the container through the discharge port thereof;

a second pressurized fluid line able to convey a pressurized fluid from a cartridge receivable within the housing over the outlet end of each liquid discharge line, the valve also able to control the flow of a pressurized fluid through the second pressurized fluid line; and the trigger, when in the first operational position, being operative to control the valve to permit a pressurized fluid to flow through the second pressurized fluid line, whereby a flow of pressurized fluid is able to pass over the outlet ends of the liquid discharge lines to generate an aerosoling action on any liquid material emanating from the outlet ends of the liquid discharge lines.

2. The self-contained, hand-held spray dispensing device of claim 1 further comprising:

a flow interrupter for controlling the passage of liquid material through each liquid discharge line;

the trigger being operatively associated with the flow interrupter, the trigger being sequentially movable from the first operational position to a second operational position, when in the second operational position the trigger being operative to open the flow interrupter to permit the passage of a liquid material through each discharge line.

3. The self-contained, hand-held spray dispensing device of claim 1 wherein the second pressurized fluid line includes a first and a second sleeve, each sleeve being disposed in surrounding relationship about the outlet end of a respective liquid discharge line.

4. The self-contained, hand-held spray dispensing device of claim 1 wherein the liquid ejecting element comprises a piston disposed on the interior of each container.

5. The self-contained, hand-held spray dispensing device of claim 1 wherein the liquid ejecting element acts on the exterior of the container.

6. A self-contained, hand-held spray dispensing device for dispensing one or more liquid material(s), the dispensing device comprising:

a container having a discharge port for each material and a piston movably disposed therein, each piston being connectable to a force transmitting yoke having a working surface thereon, each piston being responsive to a motive force imposed on the working surface of the yoke to displace within its container, thereby to cause a liquid material in that container to be ejected from the discharge port, a housing;

a first and a second liquid discharge line disposed within the housing, each liquid discharge line having an inlet end and an outlet end;

a container support arrangement able to receive and to support a first and a second liquid container within the housing such that the discharge port of each container is disposed in fluid communication with the inlet end of a liquid discharge line;

an actuator disposed within the housing, the actuator being operative to apply a motive force to a working surface of a yoke receivable within the actuator;

a cartridge support arrangement disposed within the housing, the cartridge support arrangement being able to receive and to support a cartridge holding a pressurized motive fluid;

a first pressurized fluid line able to convey a pressurized motive fluid from a cartridge receivable within the housing into the actuator;

a valve able to control the flow of a pressurized motive fluid through the first pressurized fluid line; and a trigger operatively associated with the valve, the trigger being movable from a rest position to a first operational position, when in the first operational position the trigger being operative to open the valve to permit a pressurized motive fluid from a cartridge receivable within the housing to flow through the first pressurized fluid line into the actuator to generate a motive force on the working surface of a yoke receivable within the actuator, thereby to cause each piston in a container receivable in the housing to eject a liquid in the container through the discharge port thereof;

a second pressurized fluid line able to convey a pressurized fluid from a cartridge receivable within the housing over the outlet end of each liquid discharge line, the valve also able to control the flow of a pressurized fluid through the second pressurized fluid line; and the trigger, when in the first operational position, being operative to control the valve to permit a pressurized fluid to flow through the second pressurized fluid line, whereby a flow of pressurized fluid is able to pass over the outlet ends of the liquid discharge lines to generate an aerosoling action on any liquid material emanating from the outlet ends of the liquid discharge lines.

7. The self-contained, hand-held spray dispensing device of claim 6 wherein at least one container having a liquid material therein is removably received by the container support arrangement.

8. The self-contained, hand-held spray dispensing device of claim 6 wherein a first and a second container each having a liquid material therein are removably received by the container support arrangement.

9. The self-contained, hand-held spray dispensing device of claim 6 wherein a cartridge having a pressurized motive fluid therein is received by the cartridge support arrangement.

10. The self-contained, hand-held spray dispensing device of claim 6 further comprising:

a flow interrupter for controlling the passage of liquid material through each liquid discharge line;

the trigger being operatively associated with the flow interrupter, the trigger being sequentially movable from the first operational position to a second operational position, when in the second operational position the trigger being operative to open the flow interrupter to permit the passage of a liquid material through each discharge line.

11. The self-contained, hand-held spray dispensing device of claim 6 further comprising:

a mounting arrangement able to receive and to hold a source containing a pressurized aerosoling fluid within the housing;

the second pressurized fluid line able to convey a pressurized aerosoling fluid from a source receivable within the housing over the outlet end of each liquid discharge line, the valve able to control the flow of a pressurized aerosoling fluid through the pressurized fluid line; and the trigger, when in the first operational position, being operative to control the valve to permit a pressurized aerosoling fluid to flow through the second pressurized fluid line, whereby a flow of pressurized aerosoling fluid is able to pass over the outlet ends of the liquid discharge lines to generate an aerosoling action on any liquid material emanating from the outlet ends of the liquid discharge lines.

12. The self-contained, hand-held spray dispensing device of claim 11 wherein a single cartridge receivable in the housing is able to provide both a pressurized motive fluid and a pressurized aerosoling fluid.

13. The self-contained, hand-held spray dispensing device of claim 12 wherein the same valve is able to act to control a pressurized fluid flow through both the first and second pressurized fluid lines.

14. The self-contained, hand-held spray dispensing device of claim 11 wherein the second pressurized fluid line includes a first and a second sleeve, each sleeve being disposed in surrounding relationship about the outlet end of a respective liquid discharge line.

15. The self-contained, hand-held spray dispensing device of claim 6 further comprising a regulator for supplying a regulated flow of pressurized fluid to the valve.

16. A self-contained, hand-held spray dispensing device for dispensing one or more liquid material(s), the dispensing device comprising:

a container having a discharge port for each material and a piston movably disposed therein, each piston being connectable to a force transmitting yoke having a working surface thereon, each piston being responsive to a motive force imposed on the working surface of the yoke to displace within its container, thereby to cause a liquid material in that container to be ejected from the discharge port, a housing;

a first and a second liquid discharge line disposed within the housing, the each liquid discharge line having an inlet end and an outlet end;

a container support arrangement able to receive and to support a first and a second liquid container within the housing such that the discharge port of each container is disposed in fluid communication with the inlet end of a liquid discharge line;

an actuator disposed within the housing, the actuator being operative to apply a motive force to a working surface of a yoke receivable within the actuator;

a cartridge support arrangement disposed within the housing, the cartridge support arrangement being able to receive and to support a cartridge holding a pressurized fluid;

a first pressurized fluid line and a second pressurized fluid line, the pressurized fluid lines being able to convey a pressurized fluid from a cartridge receivable within the housing to the actuator and over the outlet end of each liquid discharge line, respectively;

a valve able to control the flow of a pressurized fluid through the first and second pressurized fluid lines;

a trigger operatively associated with the valve, the trigger being movable from a rest position to a first operational position, when in the first operational position the trigger being operative to open the valve to permit simultaneous pressurized fluid flow from a cartridge receivable within the housing:

(i) through the first pressurized fluid line into the actuator to generate a motive force on the working surface of a yoke receivable within the actuator; and (ii) through the second pressurized fluid line over the outlet ends of the discharge lines, thereby to cause each piston in a container receivable in the housing to eject a liquid in the container through the discharge port thereof and into the inlet end of a liquid discharge line;

the first and second pressurized fluid lines being complementarily configured with respect to each other such that:

the pressure of any fluid flowing through the first pressurized fluid line is able to act on the working surface of a yoke receivable in the actuator to impose a motive force on a piston sufficient to cause a liquid material to emanate at a predetermined rate from the outlet end of each liquid discharge line, and, simultaneously, the velocity of any fluid flowing through the second pressurized fluid line being able to act to aerosolize any liquid material emanating from the outlet ends of the discharge lines.

17. The self-contained, hand-held spray dispensing device of claim 16 further comprising:

a flow interrupter for controlling the passage of liquid material through each liquid discharge line;

the trigger operatively associated with the flow interrupter, the trigger being sequentially movable from the first position to a second position, when in the second position the trigger being operative to open the flow interrupter to permit the passage of liquid material through the liquid discharge lines, whereby flow through the second pressurized fluid line starts before and finishes after the passage of any liquid material through each liquid discharge line.

18. The self-contained, hand-held spray dispensing device of claim 16 wherein at least one container having a liquid material therein is removably received by the container support arrangement.

19. The self-contained, hand-held spray dispensing device of claim 16 wherein a first and a second container each having a liquid material therein are removably received by the container support arrangement.

20. The self-contained, hand-held spray dispensing device of claim 16 wherein a cartridge having a pressurized fluid therein is received by the cartridge support arrangement.

21. The self-contained, hand-held spray dispensing device of claim 16 wherein the cartridge support arrangement includes a door closure that has an over-center cam mechanism associated therewith, the cam mechanism being responsive to a force produced by a pressurized fluid in a cartridge for imposing a biasing force to maintain the door in the closed position.

22. The self-contained, hand-held spray dispensing device of claim 16 wherein the second pressurized fluid line includes a first and a second sleeve, each sleeve being disposed in surrounding relationship about the outlet end of a respective liquid discharge line.

23. A self-contained, hand-held spray dispensing device for dispensing one or more liquid material(s), the dispensing device comprising:

a container having a discharge port for each material and a piston movably disposed therein, each piston being connectable to a force transmitting yoke, each piston being responsive to a motive force imposed on the yoke to displace within its container, thereby to cause a liquid material in that container to be ejected from the discharge port, a housing;

a first and a second liquid discharge line disposed within the housing, each liquid discharge line having an inlet end and an outlet end;

a container support arrangement able to receive and to support a first and a second liquid container within the housing such that the discharge port of each container is disposed in fluid communication with the inlet end of a liquid discharge line;

an actuator disposed within the housing, the actuator including an actuating element operative to apply a motive force to a yoke receivable within the housing;

a cartridge support arrangement disposed within the housing, the cartridge support arrangement being able to receive and to support a cartridge holding a pressurized motive fluid;

a pressurized fluid line able to convey a pressurized fluid from a cartridge receivable within the housing able over the outlet end of each liquid discharge line;

a valve able to control the flow of a pressurized fluid through the pressurized fluid line; and a trigger operatively associated with the valve, the trigger being movable from a rest position to a first operational position, when in the first operational position the trigger being operative to open the valve to permit a pressurized fluid from a cartridge receivable within the housing to flow through the pressurized fluid line over the outlet ends of the discharge lines;

a second pressurized fluid line able to convey a pressurized fluid from a cartridge receivable within the housing over the outlet end of each liquid discharge line, the valve also able to control the flow of a pressurized fluid through the second pressurized fluid line; and the trigger, when in the first operational position, being operative to control the valve to permit a pressurized fluid to flow through the second pressurized fluid line, whereby a flow of pressurized fluid is able to pass over the outlet ends of the liquid discharge lines to generate an aerosoling action on any liquid material emanating from the outlet ends of the liquid discharge lines.

24. The self-contained, hand-held spray dispensing device of claim 23 wherein the actuating element comprises a spring.

25. A self-contained, hand-held spray dispensing device for dispensing one or more liquid material(s), the dispensing device comprising:

a container having a discharge port for each material and a piston movably disposed therein, each piston being connectable to a force transmitting yoke, each piston being responsive to a motive force imposed on the yoke to displace within its container, thereby to cause a liquid material in that container to be ejected from the discharge port, a housing;

a first and a second liquid discharge line disposed within the housing, each liquid discharge line having an inlet end and an outlet end;

a container support arrangement able to receive and to support a first and a second liquid container within the housing such that the discharge port of each container is disposed in fluid communication with the inlet end of a liquid discharge line;

an electrically powered actuator disposed within the housing, the actuator being operative to apply a motive force to a yoke receivable within the housing;

a cartridge support arrangement disposed within the housing, the cartridge support arrangement being able to receive and to support a cartridge holding a pressurized motive fluid;

a pressurized fluid line able to convey a pressurized fluid from a cartridge receivable within the housing able over the outlet end of each liquid discharge line;

a valve able to control the flow of a pressurized fluid through the pressurized fluid line; and a trigger operatively associated with the valve, the trigger being movable from a rest position to a first operational position, when in the first operational position the trigger being operative to open the valve to permit a pressurized fluid from a cartridge receivable within the housing to flow through the pressurized fluid line over the outlet ends of the discharge lines;

a second pressurized fluid line able to convey a pressurized fluid from a cartridge receivable within the housing over the outlet end of each liquid discharge line, the valve also able to control the flow of a pressurized fluid through the second pressurized fluid line; and the trigger, when in the first operational position, being operative to control the valve to permit a pressurized fluid to flow through the second pressurized fluid line, whereby a flow of pressurized fluid is able to pass over the outlet ends of the liquid discharge lines to generate an aerosoling action on any liquid material emanating from the outlet ends of the liquid discharge lines.

* * * * *